United States Patent
Aranyi et al.

(10) Patent No.: US 10,166,027 B2
(45) Date of Patent: Jan. 1, 2019

(54) APPARATUS FOR APPLYING SURGICAL CLIPS

(71) Applicant: Covidien LP, Mansfield, MA (US)

(72) Inventors: Ernest Aranyi, Easton, CT (US); Kenneth H. Whitfield, New Haven, CT (US); Gregory Sorrentino, Wallingford, CT (US); Jeremy Li, Fairfield, CT (US)

(73) Assignee: Covidien LP, Mansfield, MA (US)

( * ) Notice: Subject to any disclaimer, the term of this patent is extended or adjusted under 35 U.S.C. 154(b) by 123 days.

(21) Appl. No.: 15/338,863

(22) Filed: Oct. 31, 2016

(65) Prior Publication Data

US 2017/0049449 A1    Feb. 23, 2017

Related U.S. Application Data

(60) Continuation of application No. 14/072,010, filed on Nov. 5, 2013, now Pat. No. 9,480,477, which is a
(Continued)

(51) Int. Cl.
*A61B 17/10* (2006.01)
*A61B 17/128* (2006.01)
*A61B 17/00* (2006.01)

(52) U.S. Cl.
CPC .......... *A61B 17/105* (2013.01); *A61B 17/10* (2013.01); *A61B 17/1285* (2013.01); *A61B 2017/00407* (2013.01)

(58) Field of Classification Search
CPC ... A61B 17/105; A61B 17/10; A61B 17/1285; A61B 17/12; A61B 17/122; A61B 17/128; A61B 2017/12004
See application file for complete search history.

(56) References Cited

U.S. PATENT DOCUMENTS 3,120,230 A    2/1964  Skold
3,363,628 A    1/1968  Wood
(Continued)

FOREIGN PATENT DOCUMENTS

AU    2010200641 A1    10/2010
CA    2740831 A1    4/2010
(Continued)

OTHER PUBLICATIONS

Japanese Office Action corresponding to JP 2013-225272 dated May 1, 2015.
(Continued)

*Primary Examiner* — Tuan V Nguyen

(57) ABSTRACT

An apparatus for applying surgical clips has a body portion housing a clip stack and a pair of jaws supported at a distal end of the body portion. The body portion includes a camming member, a clip follower and a lockout member having a plurality of stop members. The lockout member is movable from a first position in slidable relation to the camming member to a second position interlocked with the camming member. The camming member has at least one notch, and in a second position the lockout member has at least one of the stop members positioned to interface with the at least one notch. The engagement between the stop member and the notch limits distal movement of the camming member. The clip follower actuates the lockout member when the clip follower advances to a predetermined clip in the clip stack.

19 Claims, 29 Drawing Sheets

Related U.S. Application Data continuation of application No. 13/358,542, filed on Jan. 26, 2012, now Pat. No. 8,603,109, which is a division of application No. 11/872,750, filed on Oct. 16, 2007, now Pat. No. 8,128,643.

(60) Provisional application No. 60/852,143, filed on Oct. 17, 2006.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,449,531 A | 5/1984 | Cerwin et al. |
| 4,478,220 A | 10/1984 | Di Giovanni et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,592,498 A | 6/1986 | Braun et al. |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,951,860 A | 8/1990 | Peters et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |

(56) References Cited

U.S. PATENT DOCUMENTS

| | | |
|---|---|---|
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,045,560 A | 4/2000 | McKean et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |

(56) References Cited

U.S. PATENT DOCUMENTS

| | | |
|---|---|---|
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brook et al. |
| 7,214,232 B2 | 5/2007 | Bowman et al. |
| 7,223,271 B2 | 5/2007 | Muramatsu et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,552,853 B2 | 6/2009 | Mas et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,248 B2 | 6/2010 | Smith et al. |
| 7,731,724 B2 | 6/2010 | Huitema et al. |
| 7,740,641 B2 | 6/2010 | Huitema |
| 7,752,853 B2 | 7/2010 | Singh et al. |
| 7,753,250 B2 | 7/2010 | Clauson et al. |
| 7,766,207 B2 | 8/2010 | Mather et al. |
| 7,819,886 B2 | 10/2010 | Whitfield et al. |
| 7,887,553 B2 | 2/2011 | Lehman et al. |
| 7,905,890 B2 | 3/2011 | Whitfield et al. |
| 7,942,885 B2 | 5/2011 | Sixto, Jr. et al. |
| 7,952,060 B2 | 5/2011 | Watanabe et al. |
| 7,963,433 B2 | 6/2011 | Whitman et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |

(56) References Cited

U.S. PATENT DOCUMENTS

| | | |
|---|---|---|
| 8,070,760 B2 | 12/2011 | Fujita |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,308,743 B2 | 11/2012 | Matsuno et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,717 B2 | 11/2013 | Sorrentino et al. |
| 8,603,109 B2 | 12/2013 | Aranyi et al. |
| 8,609,109 B2 | 12/2013 | Donnelly et al. |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,920,438 B2 | 12/2014 | Aranyi et al. |
| 8,950,646 B2 | 2/2015 | Viola |
| 8,961,542 B2 | 2/2015 | Whitfield et al. |
| 8,968,337 B2 | 3/2015 | Whitfield et al. |
| 8,968,342 B2 | 3/2015 | Wingardner, III et al. |
| 8,973,804 B2 | 3/2015 | Hess |
| 9,011,464 B2 | 4/2015 | Zammataro |
| 9,011,465 B2 | 4/2015 | Whitfield et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,282,961 B2 | 3/2016 | Whitman et al. |
| 9,326,776 B2 | 5/2016 | Gadberry et al. |
| 9,358,011 B2 | 6/2016 | Sorrentino et al. |
| 9,370,400 B2 | 6/2016 | Parihar |
| 9,393,024 B2 | 7/2016 | Whitfield et al. |
| 9,398,917 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,480,477 B2 | 11/2016 | Aranyi et al. |
| 9,498,227 B2 | 11/2016 | Zergiebel et al. |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,642,627 B2 | 5/2017 | Zammataro |
| 9,687,247 B2 | 6/2017 | Aranyi et al. |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |

(56) References Cited

U.S. PATENT DOCUMENTS

| | | |
|---|---|---|
| 2003/0114867 A1 | 6/2003 | Bolduc |
| 2003/0135224 A1 | 7/2003 | Blake |
| 2003/0167063 A1 | 9/2003 | Kerr |
| 2003/0208231 A1 | 11/2003 | Williamson et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2005/0010242 A1 | 1/2005 | Lindsay |
| 2005/0080440 A1 | 4/2005 | Durgin et al. |
| 2005/0085830 A1 | 4/2005 | Lehman et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Dray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson et al. |
| 2006/0224165 A1 | 10/2006 | Surti |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn |
| 2007/0049948 A1 | 3/2007 | Menn |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0173866 A1 | 7/2007 | Sorrentino et al. |
| 2007/0175949 A1 | 8/2007 | Shelton et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |

(56) References Cited

U.S. PATENT DOCUMENTS

| | | |
|---|---|---|
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0103510 A1 | 5/2008 | Taylor et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0167671 A1 | 7/2008 | Giordano et al. |
| 2008/0228199 A1 | 9/2008 | Cropper et al. |
| 2008/0243145 A1 | 10/2008 | Whitfield et al. |
| 2008/0255413 A1 | 10/2008 | Zemlok et al. |
| 2008/0306492 A1 | 12/2008 | Shibata |
| 2008/0306493 A1 | 12/2008 | Shibata |
| 2008/0312665 A1 | 12/2008 | Shibata et al. |
| 2008/0312670 A1 | 12/2008 | Lutze et al. |
| 2008/0319456 A1 | 12/2008 | Hart |
| 2009/0076533 A1 | 3/2009 | Kayan et al. |
| 2009/0088777 A1 | 4/2009 | Miyagi |
| 2009/0088783 A1 | 4/2009 | Kennedy et al. |
| 2009/0171380 A1 | 7/2009 | Whiting |
| 2009/0182193 A1 | 7/2009 | Whitman et al. |
| 2009/0209946 A1 | 8/2009 | Swayze et al. |
| 2009/0222003 A1 | 9/2009 | Otley |
| 2009/0228023 A1 | 9/2009 | Gui |
| 2009/0264904 A1 | 10/2009 | Aldrich |
| 2009/0299382 A1 | 12/2009 | Zergiebel |
| 2009/0326558 A1 | 12/2009 | Cui |
| 2010/0049216 A1 | 2/2010 | Lergiebel |
| 2010/0057105 A1 | 3/2010 | Sorrentino et al. |
| 2010/0057107 A1 | 3/2010 | Sorrentino et al. |
| 2010/0069935 A1 | 3/2010 | Crainich |
| 2010/0274262 A1 | 10/2010 | Schulz et al. |
| 2010/0274264 A1 | 10/2010 | Schulz et al. |
| 2011/0054498 A1 | 3/2011 | Monassevitch et al. |
| 2011/0082474 A1 | 4/2011 | Bindra et al. |
| 2011/0087241 A1 | 4/2011 | Nguyen |
| 2011/0087242 A1 | 4/2011 | Pribanic et al. |
| 2011/0087243 A1 | 4/2011 | Nguyen et al. |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn et al. |
| 2011/0245848 A1 | 10/2011 | Rosenberg et al. |
| 2011/0251608 A1 | 10/2011 | Timm et al. |
| 2011/0295290 A1 | 12/2011 | Whitfield |
| 2011/0313437 A1 | 12/2011 | Yeh |
| 2012/0029534 A1 | 2/2012 | Whitfield et al. |
| 2012/0041455 A1 | 2/2012 | Martinez |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino et al. |
| 2012/0123446 A1 | 5/2012 | Aranyi et al. |
| 2012/0197269 A1 | 8/2012 | Zammataro |
| 2012/0265220 A1 | 10/2012 | Menn |
| 2012/0277765 A1 | 11/2012 | Zammataro et al. |
| 2012/0310259 A1 | 12/2012 | Sorrentino et al. |
| 2012/0330326 A1 | 12/2012 | Creston et al. |
| 2013/0110135 A1 | 5/2013 | Whitfield et al. |
| 2013/0131697 A1 | 5/2013 | Hartoumbekis |
| 2013/0165951 A1 | 6/2013 | Blake, III |
| 2013/0165952 A1 | 6/2013 | Whitfield et al. |
| 2013/0172909 A1 | 7/2013 | Harris |
| 2013/0172910 A1 | 7/2013 | Malkowski |
| 2013/0172911 A1 | 7/2013 | Rockrohr et al. |
| 2013/0172912 A1 | 7/2013 | Whitfield et al. |
| 2013/0190779 A1 | 7/2013 | Whitfield et al. |
| 2013/0190780 A1 | 7/2013 | Whitfield et al. |
| 2013/0253541 A1 | 9/2013 | Zergiebel |
| 2013/0274767 A1 | 10/2013 | Sorrentino et al. |
| 2013/0289583 A1 | 10/2013 | Zergiebel et al. |
| 2013/0296891 A1 | 11/2013 | Hartoumbekis |
| 2013/0296892 A1 | 11/2013 | Sorrentino et al. |
| 2013/0310849 A1 | 11/2013 | Malkowski |
| 2013/0325040 A1 | 12/2013 | Zammataro |
| 2014/0039526 A1 | 2/2014 | Malkowski |
| 2014/0052157 A1 | 2/2014 | Whitfield et al. |
| 2014/0058412 A1 | 2/2014 | Aranyi et al. |
| 2014/0194903 A1 | 7/2014 | Malkowski et al. |
| 2014/0207156 A1 | 7/2014 | Malkowski |
| 2014/0263565 A1 | 9/2014 | Lytle, IV et al. |
| 2014/0296879 A1 | 10/2014 | Menn et al. |
| 2014/0316441 A1 | 10/2014 | Zergiebel et al. |
| 2014/0330291 A1 | 11/2014 | Whitfield et al. |
| 2015/0005790 A1 | 1/2015 | Whitfield et al. |
| 2015/0032131 A1 | 1/2015 | Sorrentino et al. |
| 2015/0045816 A1 | 2/2015 | Aranyi et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |
| 2015/0164511 A1 | 6/2015 | Whitfield et al. |
| 2015/0190138 A1 | 7/2015 | Whitfield et al. |
| 2015/0190139 A1 | 7/2015 | Zammataro |
| 2015/0282808 A1 | 10/2015 | Sorrentino et al. |
| 2015/0351771 A1 | 12/2015 | Malkowski et al. |
| 2015/0351772 A1 | 12/2015 | Malkowski et al. |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0128071 A1 | 5/2017 | Holsten et al. |
| 2017/0172780 A1 | 6/2017 | Aravalli |
| 2017/0238936 A1 | 8/2017 | Mujawar |
| 2017/0258472 A1 | 9/2017 | Aranyi |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |

(56) References Cited

U.S. PATENT DOCUMENTS

2018/0116675 A1    5/2018   Baril
2018/0116676 A1    5/2018   Williams

FOREIGN PATENT DOCUMENTS

| | | |
|---|---|---|
| CN | 101401737 A | 4/2009 |
| CN | 100571640 C | 12/2009 |
| CN | 101664329 A | 3/2010 |
| DE | 202009006113 U1 | 7/2009 |
| EP | 0000756 A1 | 2/1979 |
| EP | 0073655 A1 | 3/1983 |
| EP | 0085931 A2 | 8/1983 |
| EP | 0086721 A2 | 8/1983 |
| EP | 0089737 A1 | 9/1983 |
| EP | 0092300 A1 | 10/1983 |
| EP | 0324166 A2 | 7/1989 |
| EP | 0392750 A1 | 10/1990 |
| EP | 0406724 A1 | 1/1991 |
| EP | 0409569 A1 | 1/1991 |
| EP | 0514139 A3 | 3/1993 |
| EP | 0569223 A1 | 11/1993 |
| EP | 0594003 A1 | 4/1994 |
| EP | 0598529 A2 | 5/1994 |
| EP | 0685204 A1 | 12/1995 |
| EP | 0732078 A2 | 9/1996 |
| EP | 0755655 A2 | 1/1997 |
| EP | 0769274 A1 | 4/1997 |
| EP | 0769275 A1 | 4/1997 |
| EP | 0834286 A1 | 4/1998 |
| EP | 1317906 A1 | 6/2003 |
| EP | 1 468 653 A2 | 10/2004 |
| EP | 1609427 A1 | 12/2005 |
| EP | 1712187 A2 | 10/2006 |
| EP | 1712191 A2 | 10/2006 |
| EP | 1757236 A2 | 2/2007 |
| EP | 1 813 207 A1 | 8/2007 |
| EP | 1813199 A1 | 8/2007 |
| EP | 1894531 A2 | 3/2008 |
| EP | 1908423 A2 | 4/2008 |
| EP | 1913881 A1 | 4/2008 |
| EP | 1939231 A1 | 7/2008 |
| EP | 2 000 102 A2 | 12/2008 |
| EP | 2 140 817 A1 | 1/2010 |
| EP | 2229895 A1 | 9/2010 |
| EP | 2 263 570 A1 | 12/2010 |
| EP | 2332471 A1 | 6/2011 |
| EP | 2412318 A2 | 2/2012 |
| GB | 1134832 A | 11/1968 |
| GB | 2073022 A | 10/1981 |
| JP | 10118083 | 5/1998 |
| JP | 2003033361 A | 2/2003 |
| JP | 2006501954 A | 1/2006 |
| JP | 2006154230 A | 6/2006 |
| JP | 2006209948 A | 8/2006 |
| JP | 2006277221 A | 10/2006 |
| JP | 2007250843 A | 9/2007 |
| JP | 2008017876 A | 1/2008 |
| JP | 2008047498 A | 2/2008 |
| JP | 2008055165 A | 3/2008 |
| JP | 2008515550 A | 5/2008 |
| JP | 2009198991 A | 9/2009 |
| JP | 5499386 B2 | 5/2014 |
| WO | 0166001 A2 | 9/2001 |
| WO | 0167965 A1 | 9/2001 |
| WO | 03086207 A1 | 10/2003 |
| WO | 03092473 A2 | 11/2003 |
| WO | 2004032762 A1 | 4/2004 |
| WO | 2005091457 A1 | 9/2005 |
| WO | 2006042076 A2 | 4/2006 |
| WO | 2006042084 A2 | 4/2006 |
| WO | 2006042110 A2 | 4/2006 |
| WO | 2006042141 A2 | 4/2006 |
| WO | 2006135479 A2 | 12/2006 |
| WO | 2008118928 A2 | 10/2008 |
| WO | 2008127968 A2 | 10/2008 |

OTHER PUBLICATIONS

European Office Action corresponding to EP 12 152 989.5 dated May 4, 2015.
Australian Office Action corresponding to AU 2009212759 dated May 7, 2015.
Japanese Office Action corresponding to JP 2013-229070 dated May 8, 2015.
Japanese Office Action corresponding to JP 2013-229996 dated May 8, 2015.
Japanese Office Action corresponding to JP 2014-190735 dated May 27, 2015; no English translation attached—unavailable.
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
European Search Report corresponding to counterpart Int'l Application No. EP 15 15 5024.1 dated Jul. 17, 2015.
European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart In'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.
International Search Report & Written Opinion corresponding to Int'l Appln. No. PCT/CN2015/091603 dated Jul. 8, 2016.
Chinese Second Office Action corresponding to Int'l Appln. No. CN 201210586814.9 dated Jul. 18, 2016.
Chinese First Office Action corresponding to Int'l Appln. No. CN 201510093591.6 dated Jul. 25, 2016.
International Search Report & Written Opinion corresponding to Int'l Appln. No. PCT/CN20151094172 dated Aug. 4, 2016.
Canadian Office Action corresponding to Int'l Appln. No. CA 2,728,538 dated Sep. 6, 2016.
Chinese Second Office Action corresponding to Int'l Appln. No. CN 201210586826.1 dated Sep. 14, 2016.
Extended European Search Report corresponding to Int'l Appln. No. EP 16 15 0287.7 dated Oct. 4, 2016.
Chinese First Office Action corresponding to Int'l Appln. No. CN 201510205737.1 dated Nov. 1, 2016.

(56) References Cited

OTHER PUBLICATIONS

European Office Action corresponding to Int'l Appln. No. EP 08 73 2820.9 dated Nov. 3, 2016.
Extended European Search Report corresponding to Int'l Appln. No. EP 16 18 5465.8 dated Dec. 21, 2016.
Extended European Search Report corresponding to Int'l Appln. No. EP 16 18 4652.2 dated Jan. 4, 2017.
Chinese First Office Action corresponding to Int'l Appln. No. CN 201510419902.3 dated Jan. 4, 2017.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
The extended European Search Report corresponding to European Application No. EP 07 25 3905.9, completed Jan. 29, 2008; dated Feb. 7, 2008; (7 Pages).
The partial European Search Report corresponding to European Application No. EP 07 25 3807.7, completed Jul. 23, 2008; dated Aug. 1, 2008; (3 pages).
International Search Report corresponding to International Application No. PCT/US08/58185, completed Sep. 4, 2008; dated Sep. 9, 2008; (2 Pages).
The International Search Report corresponding to International Application No. PCT/US08/59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar.17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 00 2681.2, completed May 31, 2011; dated Jun. 10, 2011; (3 Pages).
The extended European Search Report corresponding to European Application No. EP 11 25 0214.1, completed May 25, 2011; dated Jun. 1, 2011; (3 Pages.).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 14, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 pp).
The Extended European Search Report corresponding to EP 12 15 2989.5, completed Apr. 9, 2013 and dated Apr. 18, 2013; (9 pp).
The Extended European Search Report corresponding to EP 08 73 2820.9, completed Jul. 2, 2013 and dated Jul. 9, 2013; (10 pp).
The Extended European Search Report corresponding to EP 13 17 2008.8, completed Aug. 14, 2013 and dated Aug. 28, 2013; (8 pp).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 13 16 6382.5, completed Nov. 19, 2013 and dated Nov. 28, 2013; (8 pp).
Extended European Search Report corresponding to EP 11 25 0194.5, completed Nov. 25, 2013 and dated Dec. 3, 2013; (8 pp).
Extended European Search Report corresponding to EP 10 25 1798.4, completed Dec. 12, 2013 and dated Jan. 2, 2014; (9 pp).
Extended European Search Report corresponding to EP 10 25 2112.7, completed Jul. 29, 2014 and dated Aug. 5, 2014; (8 pp).
Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.

(56) References Cited

OTHER PUBLICATIONS

Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.

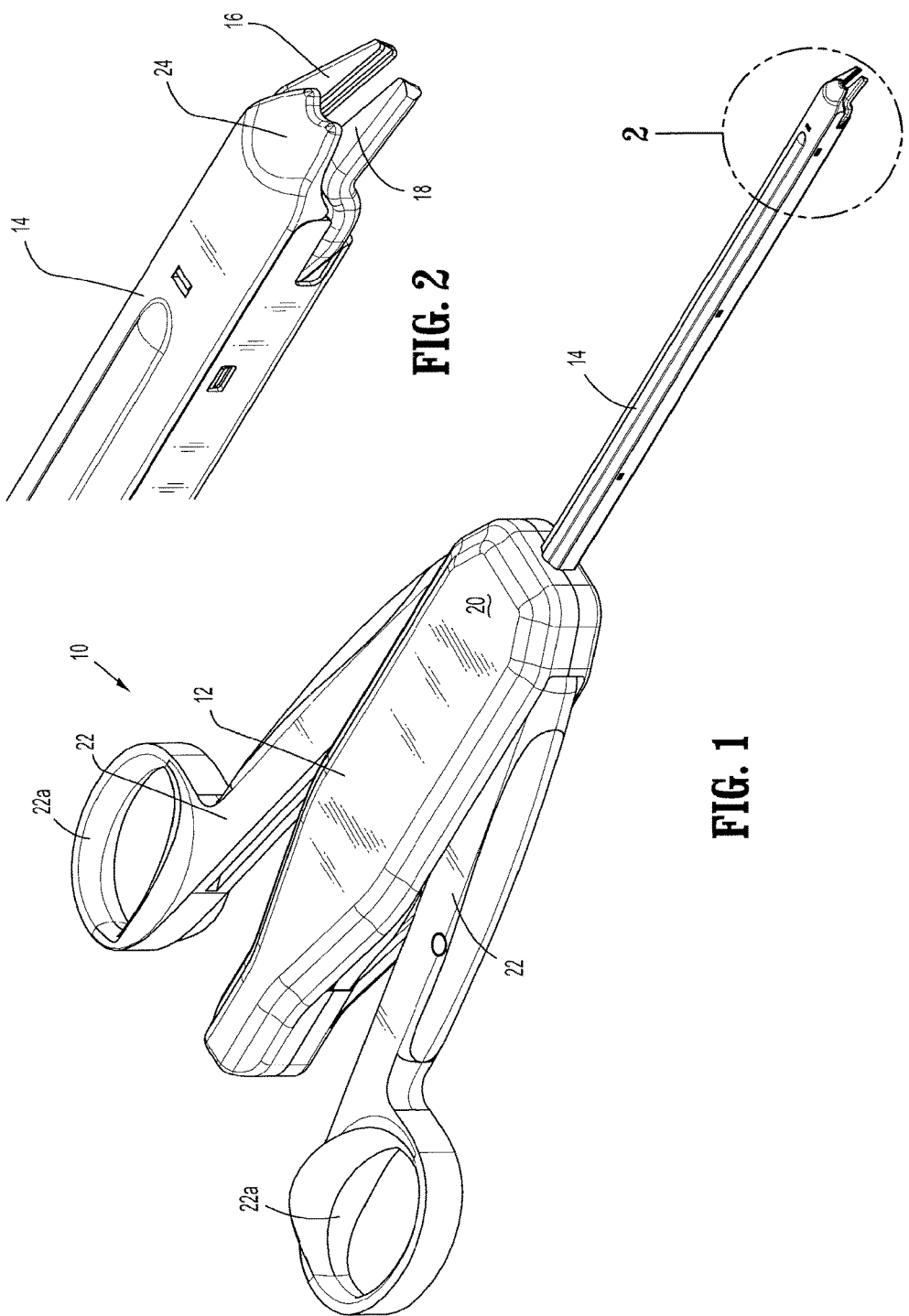

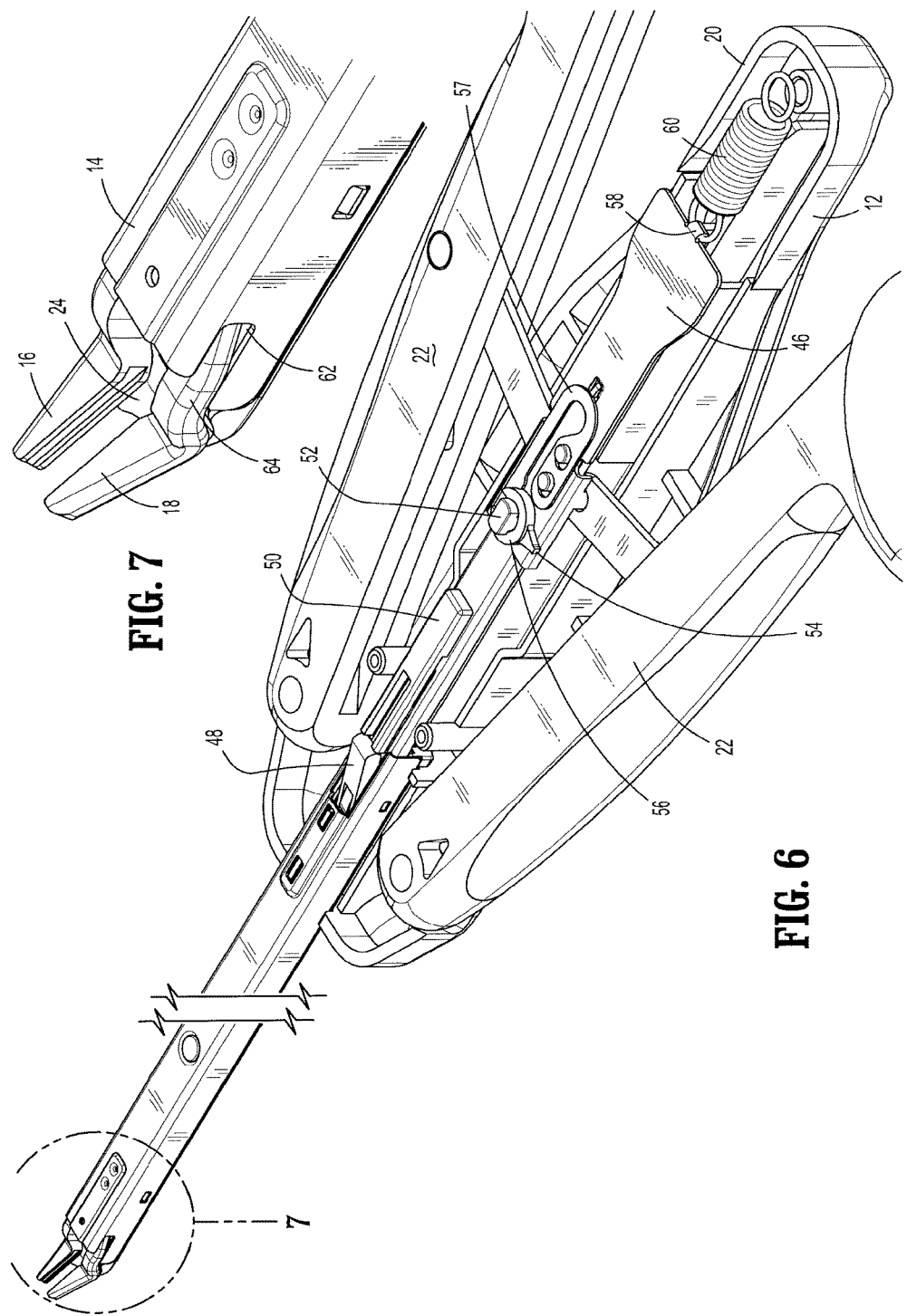

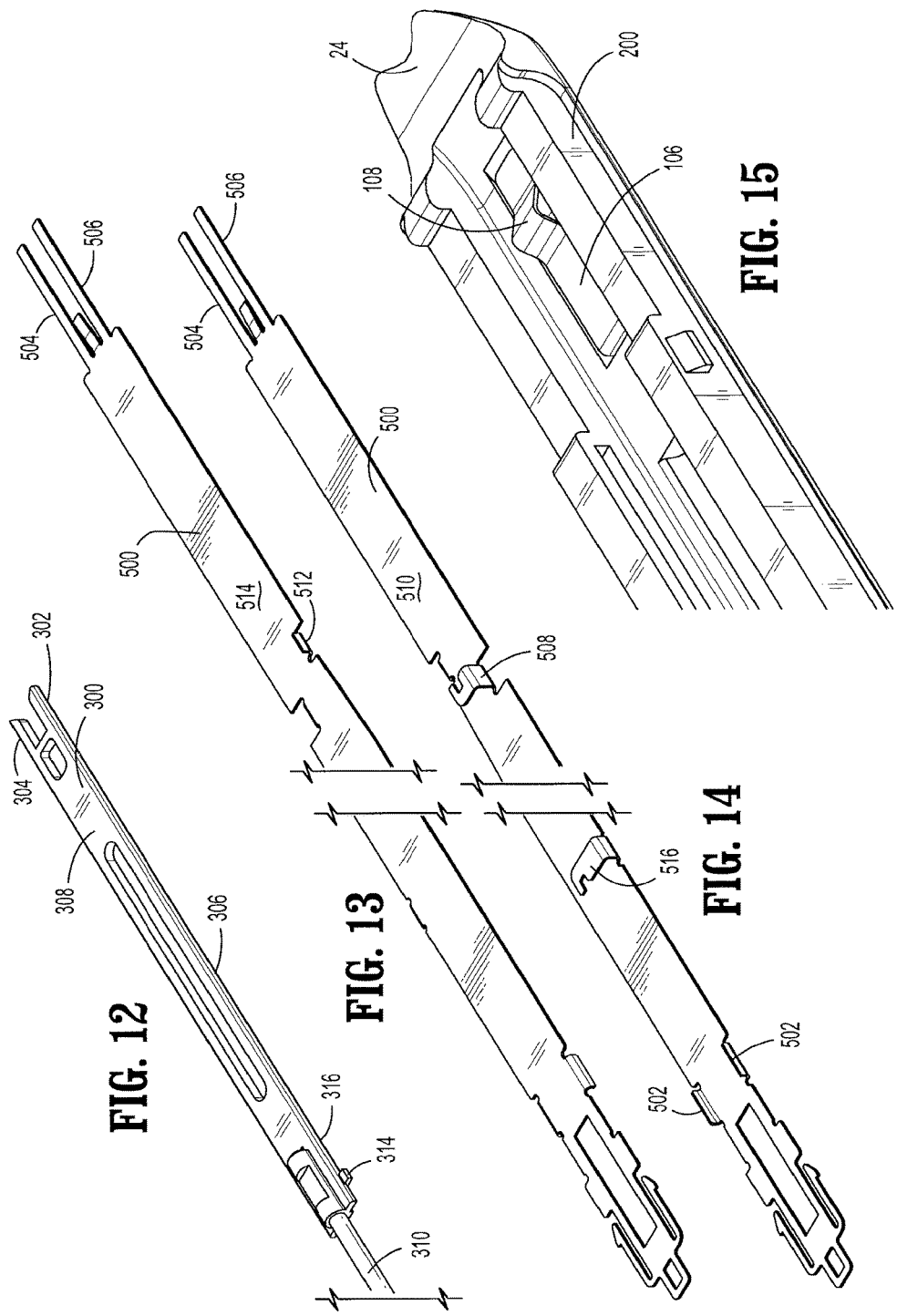

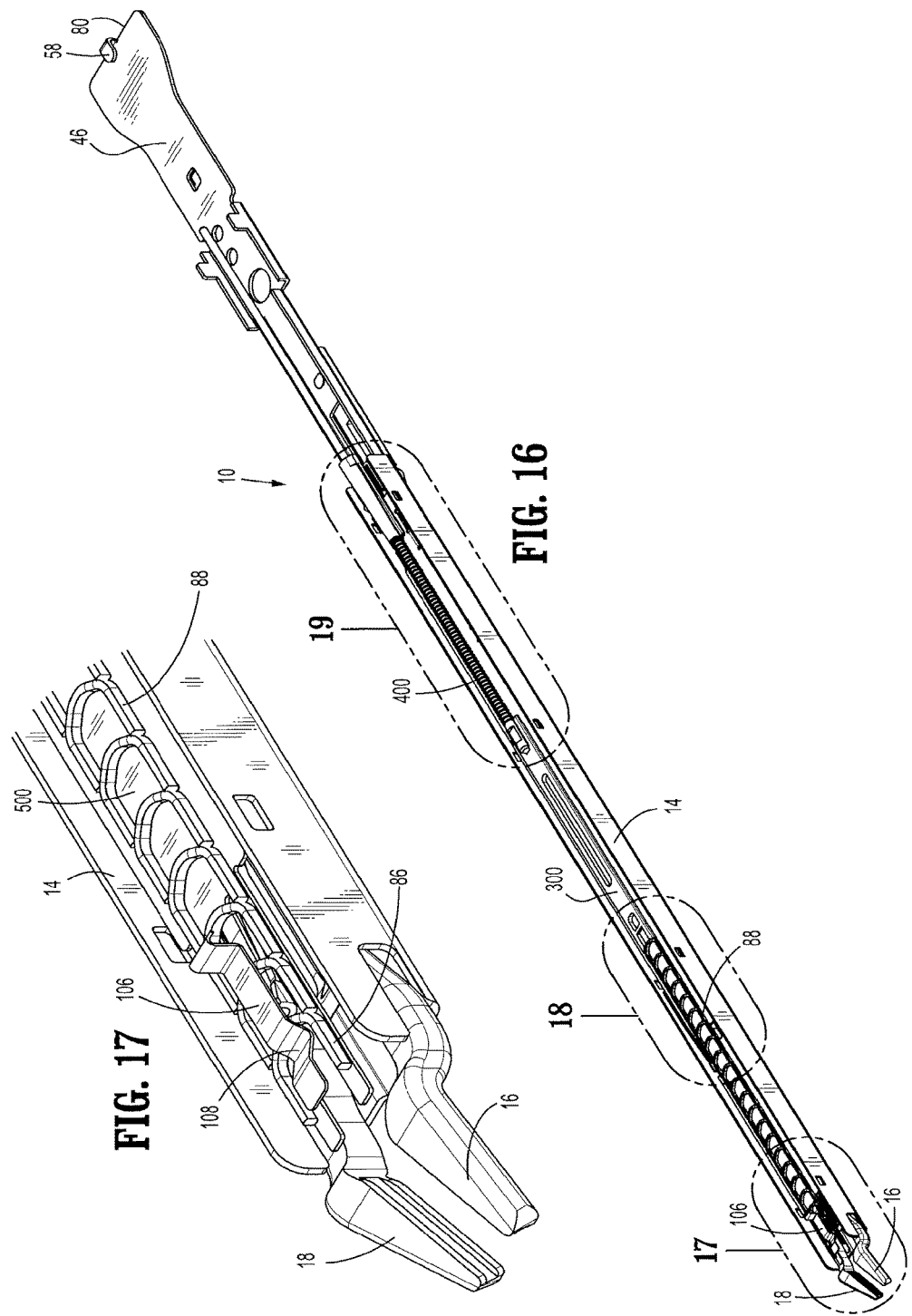

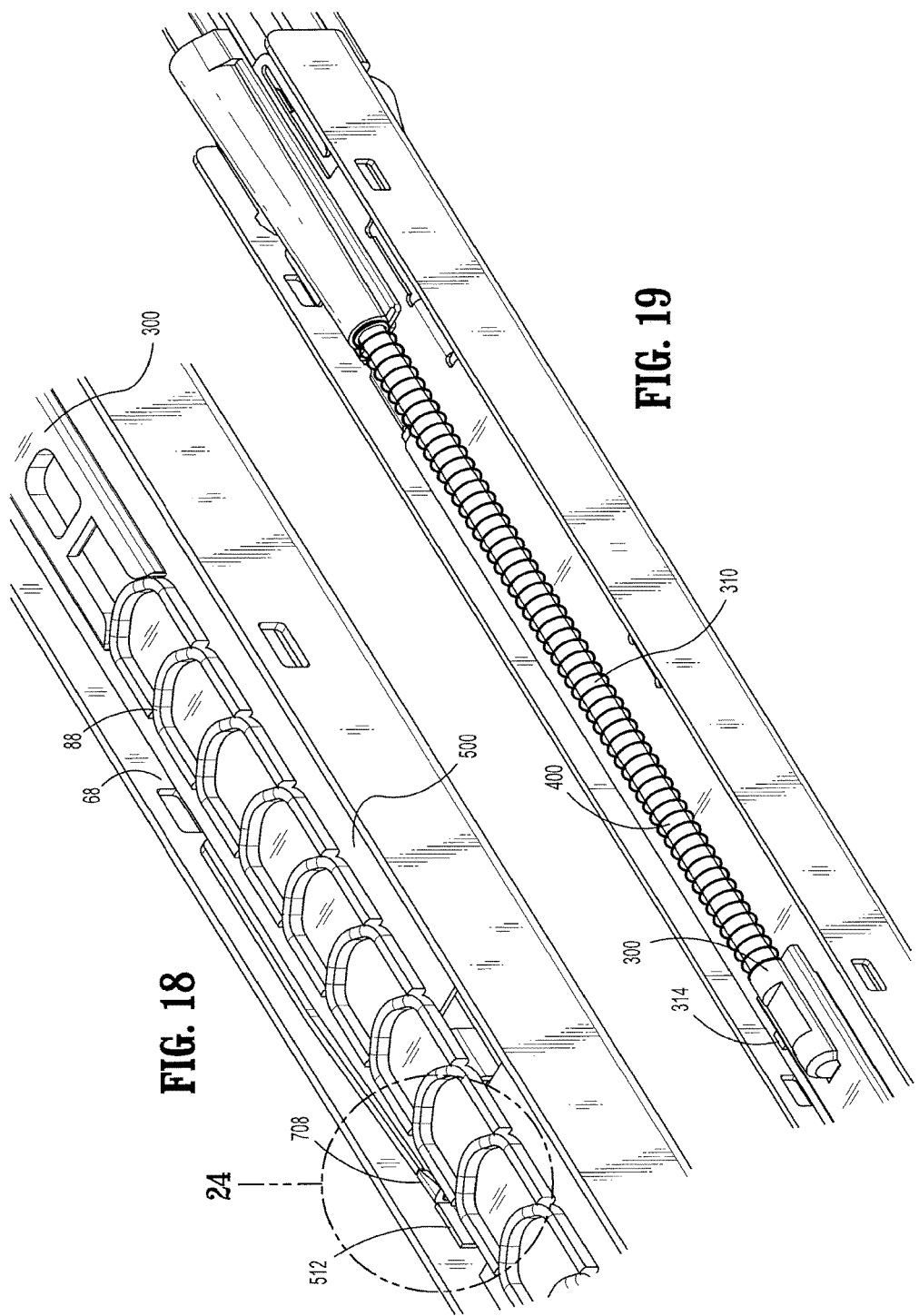

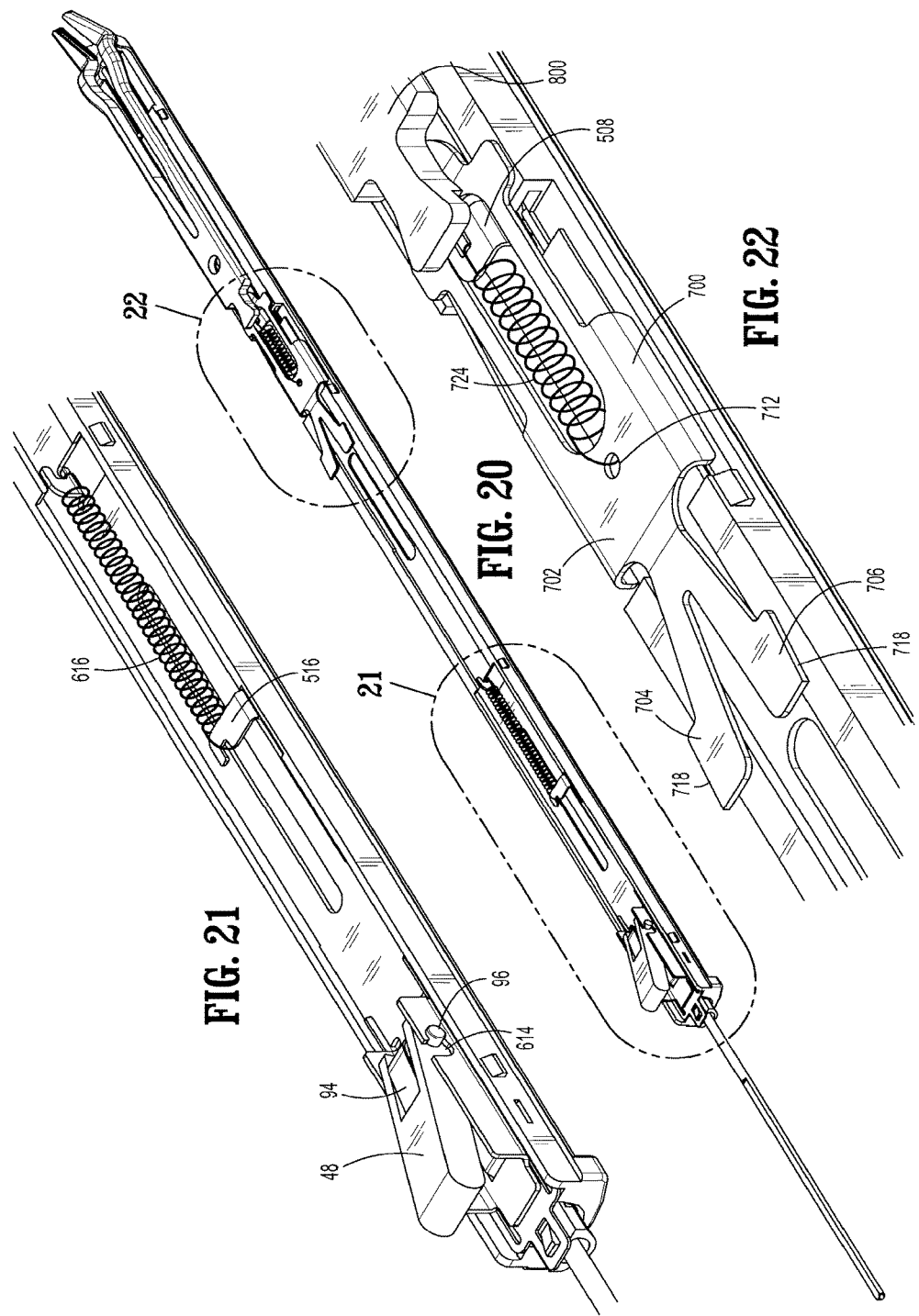

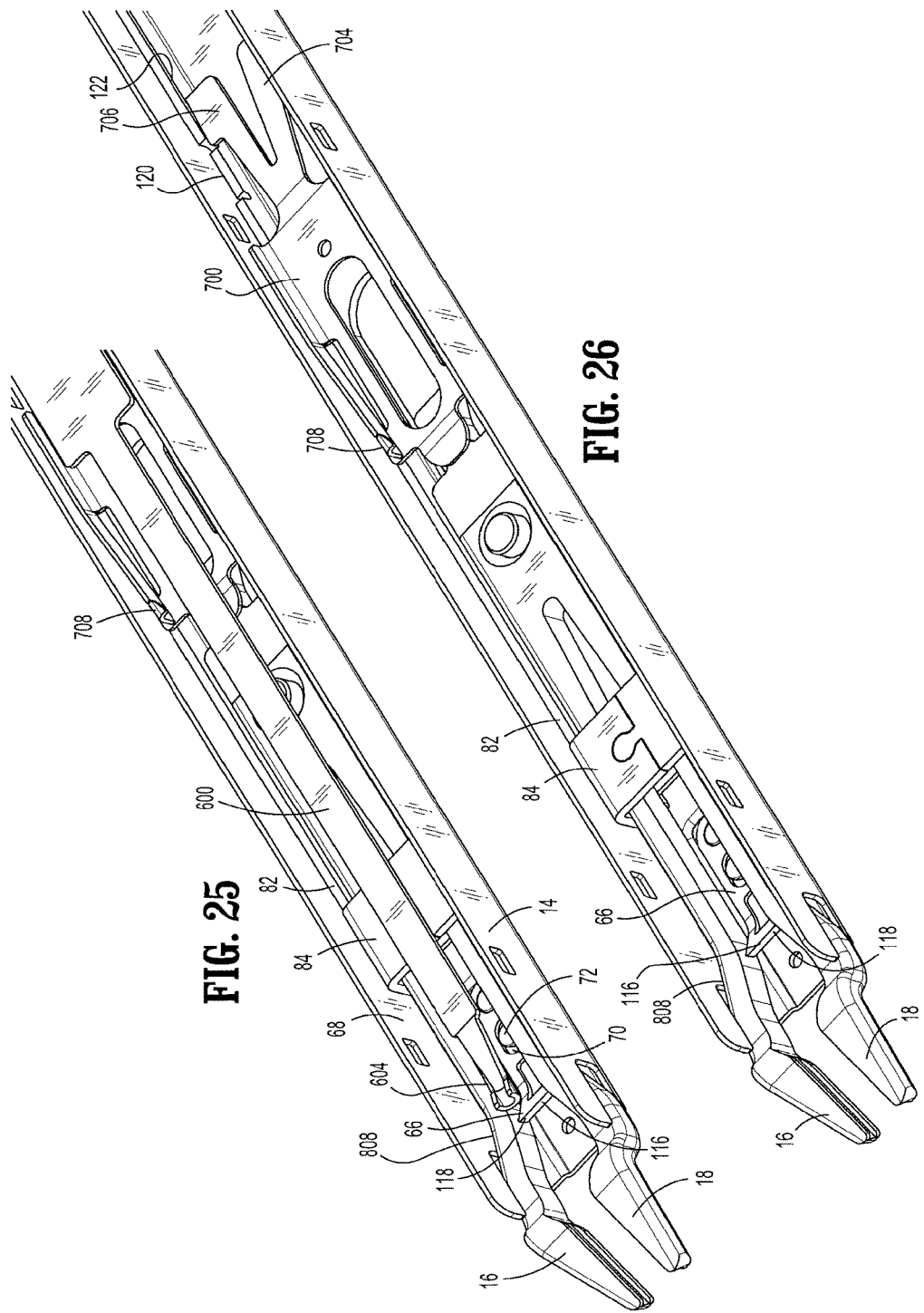

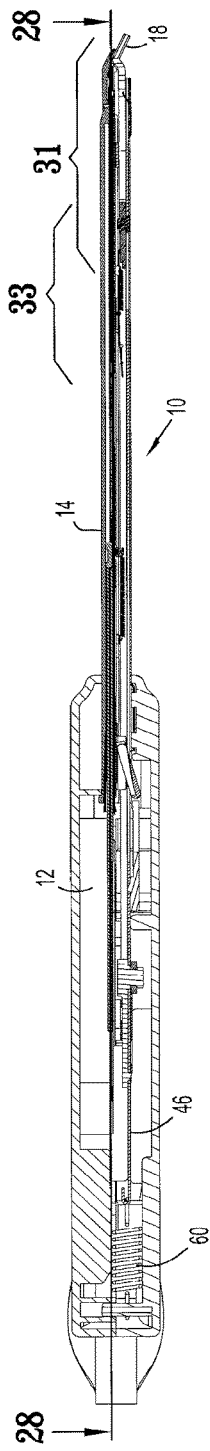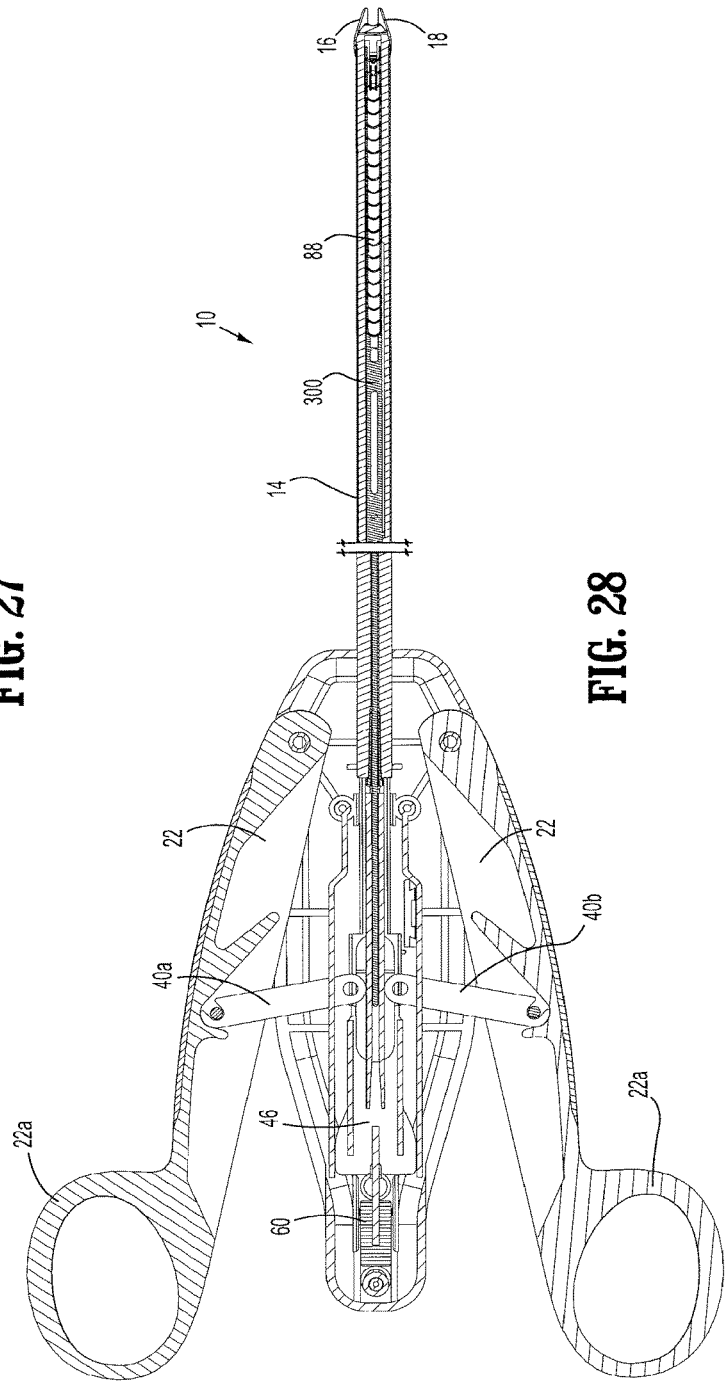
FIG. 27
FIG. 28

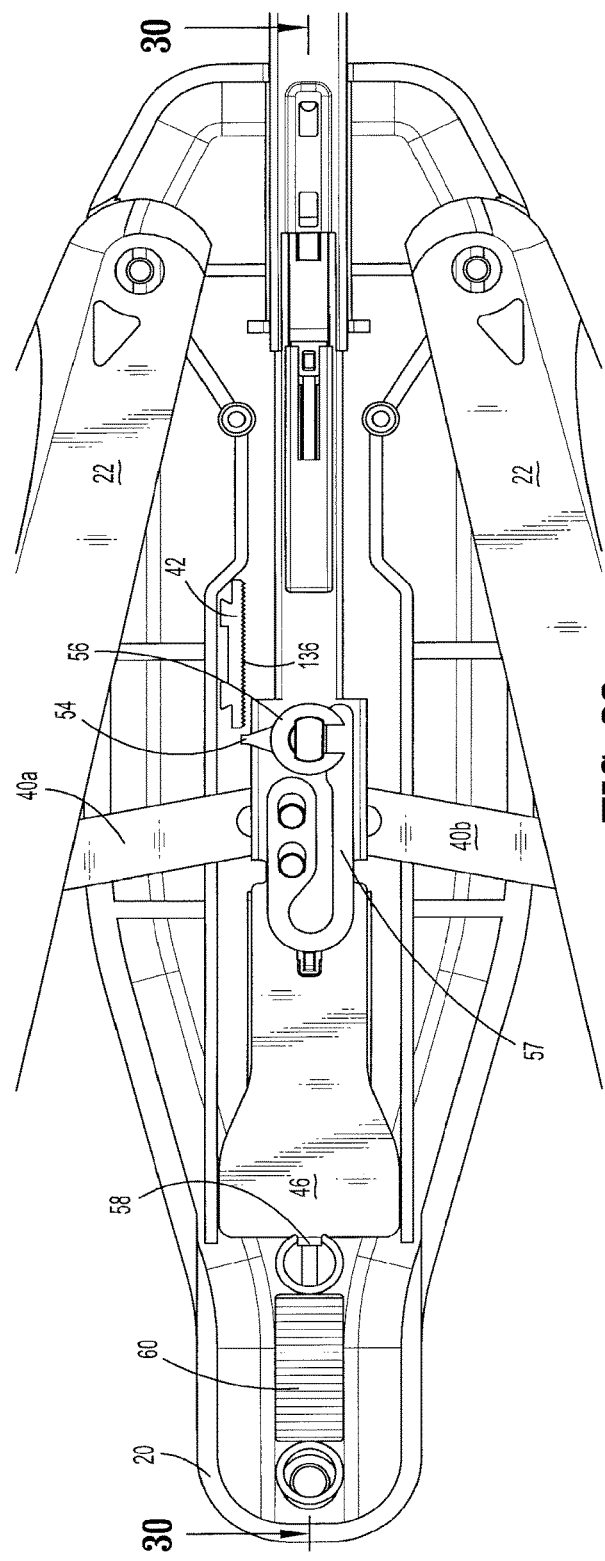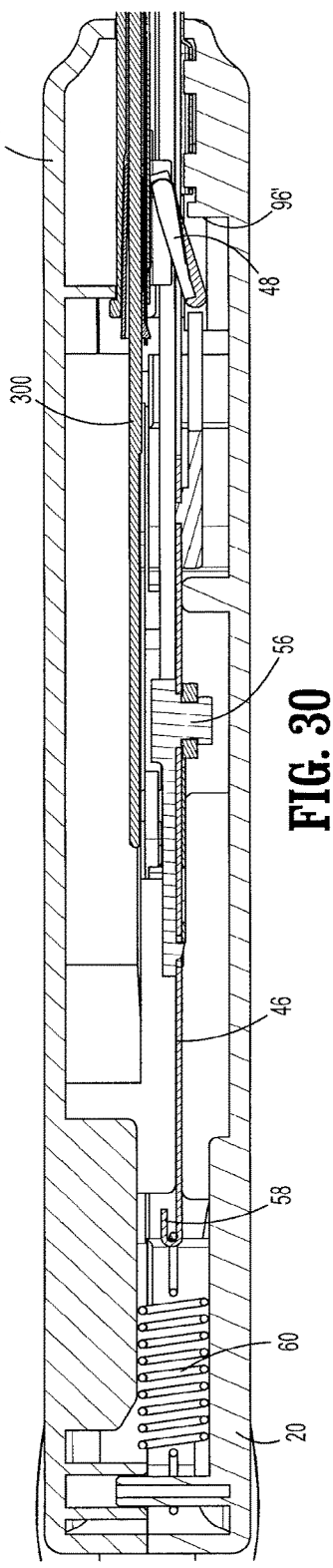
FIG. 29
FIG. 30

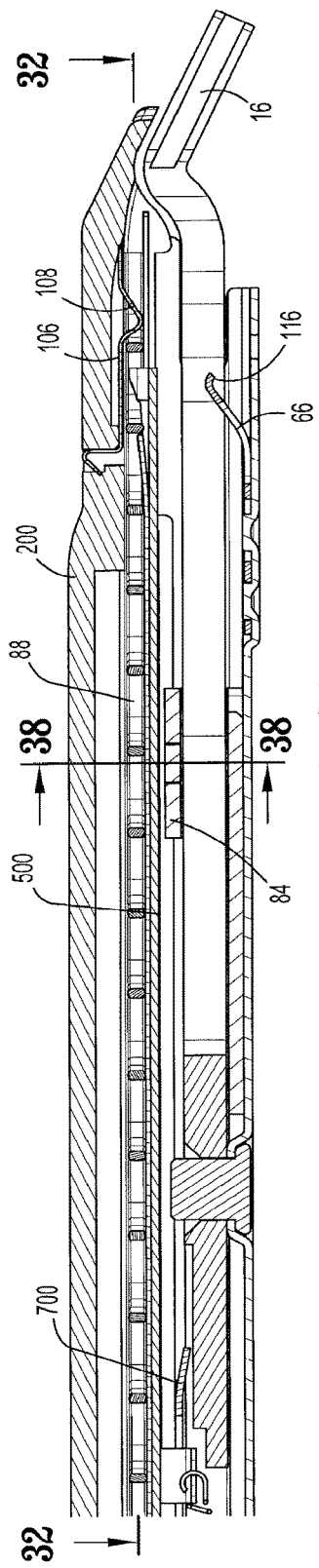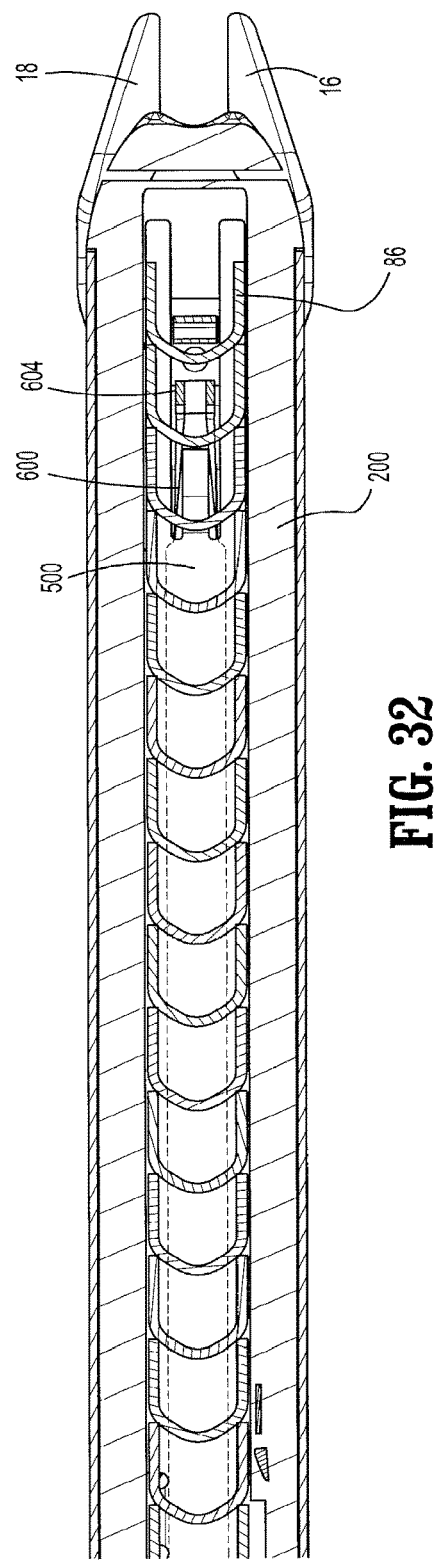
FIG. 31
FIG. 32

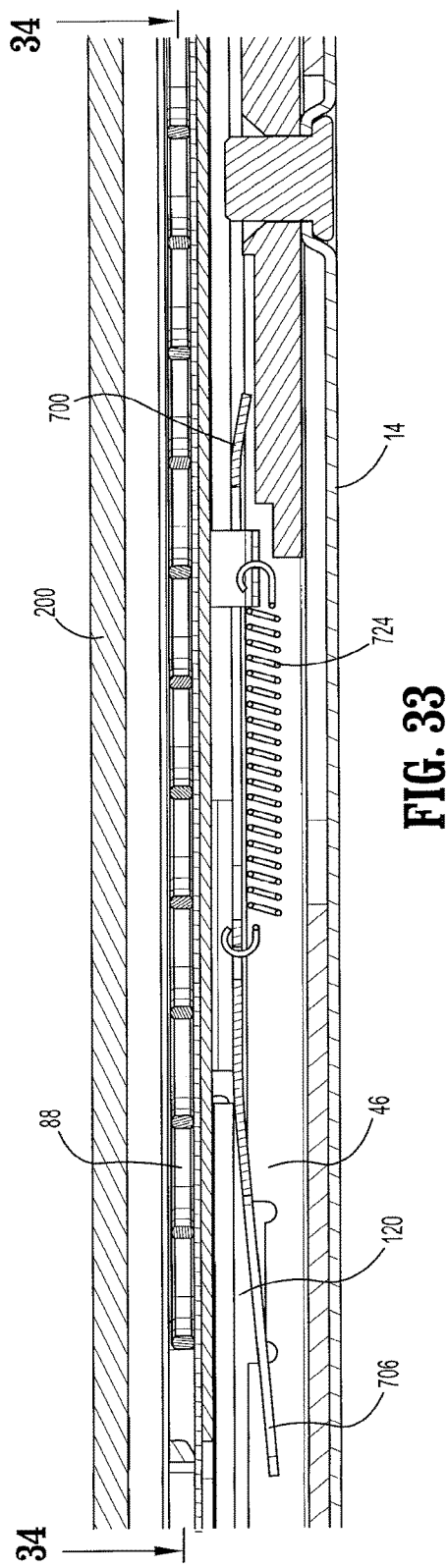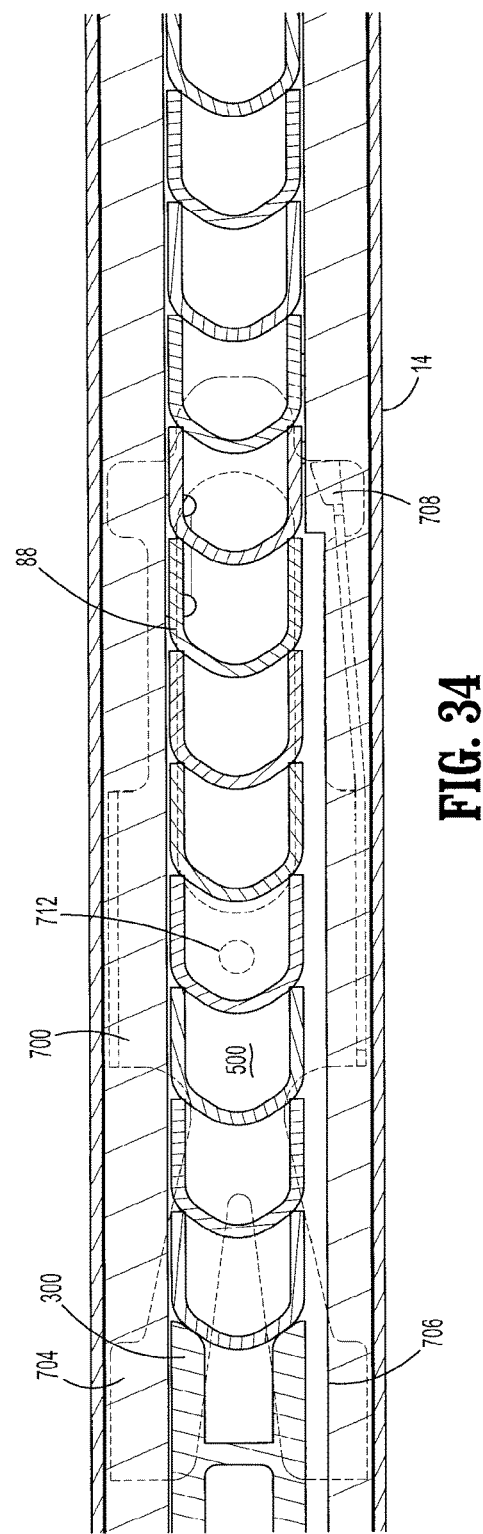

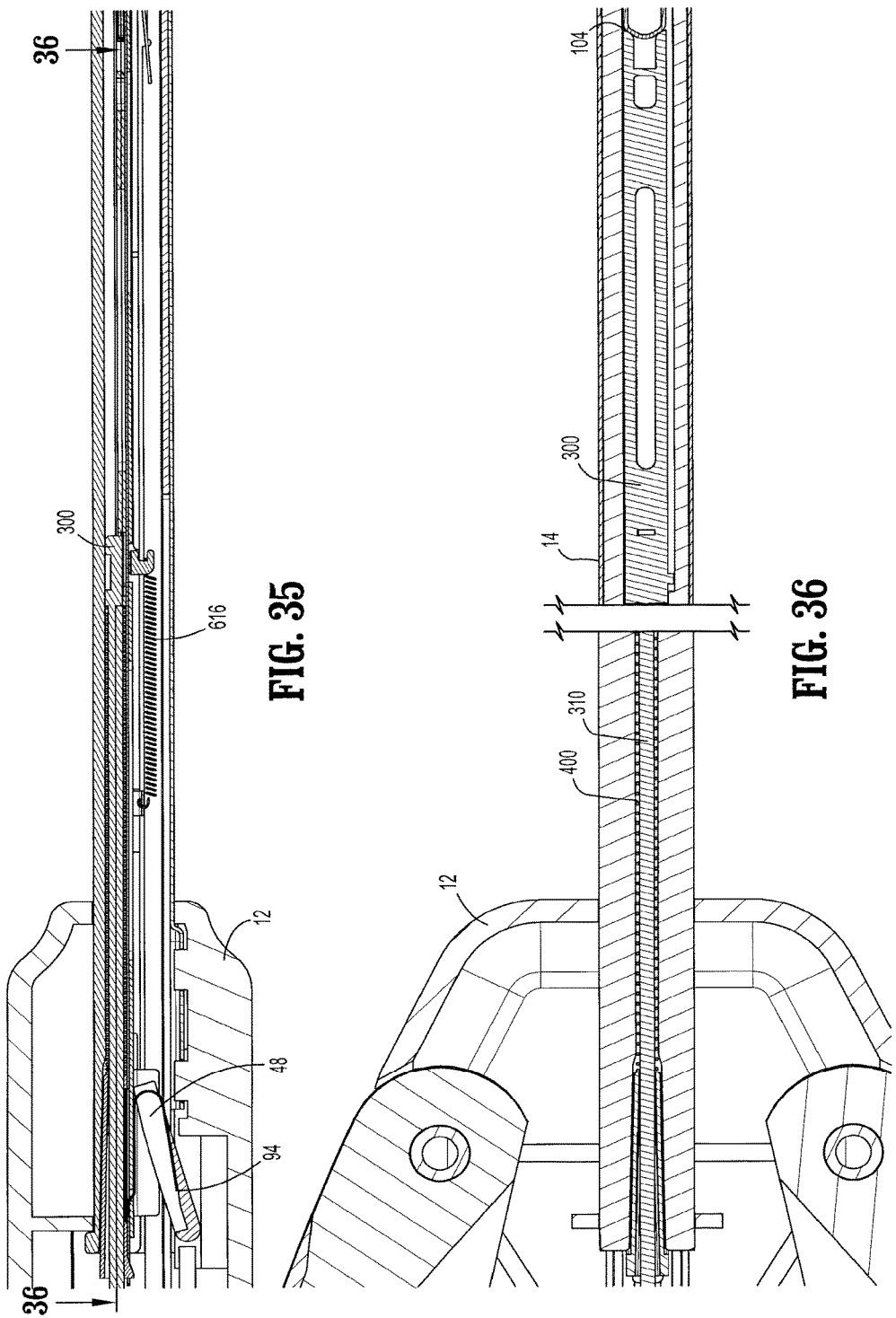

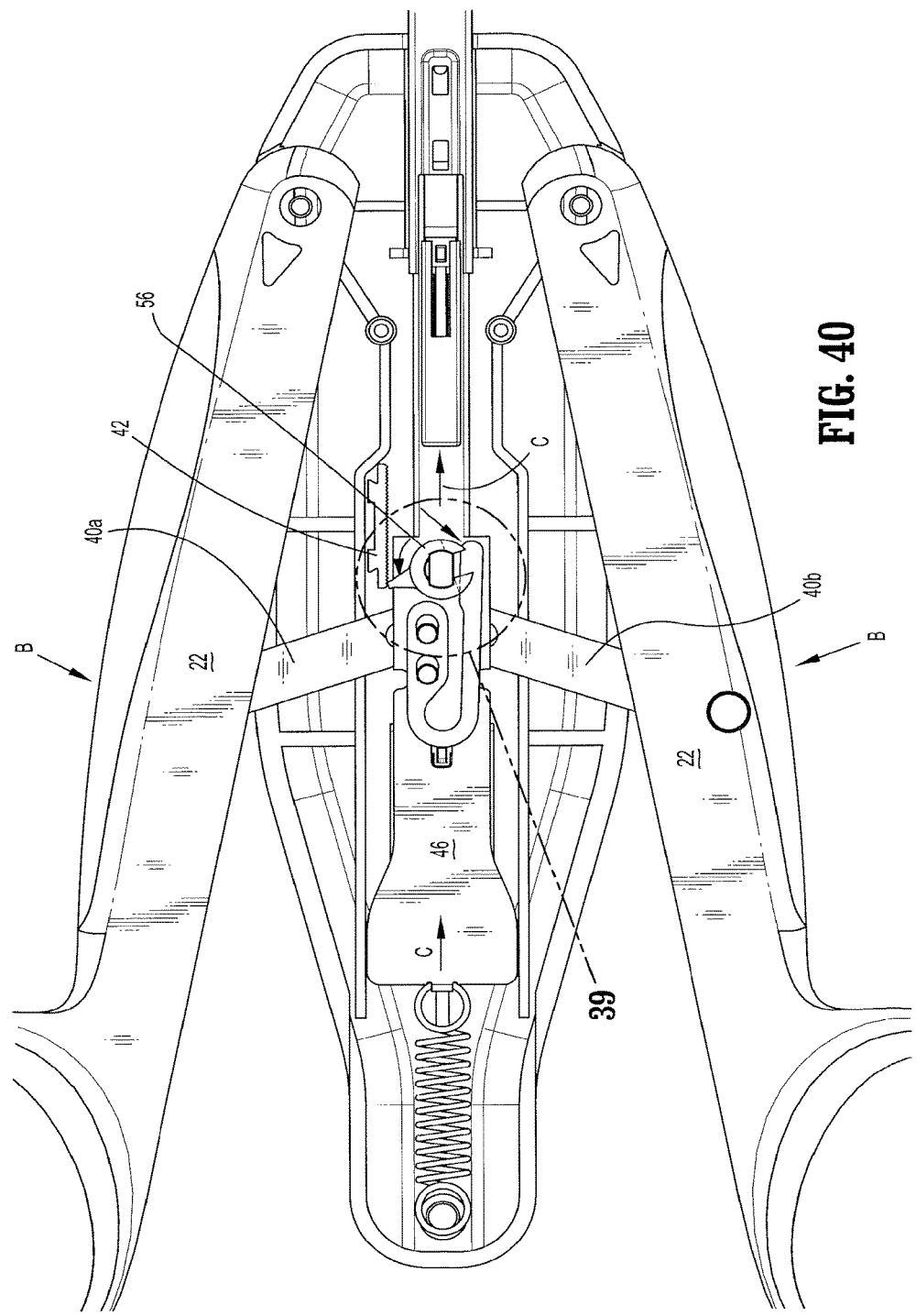

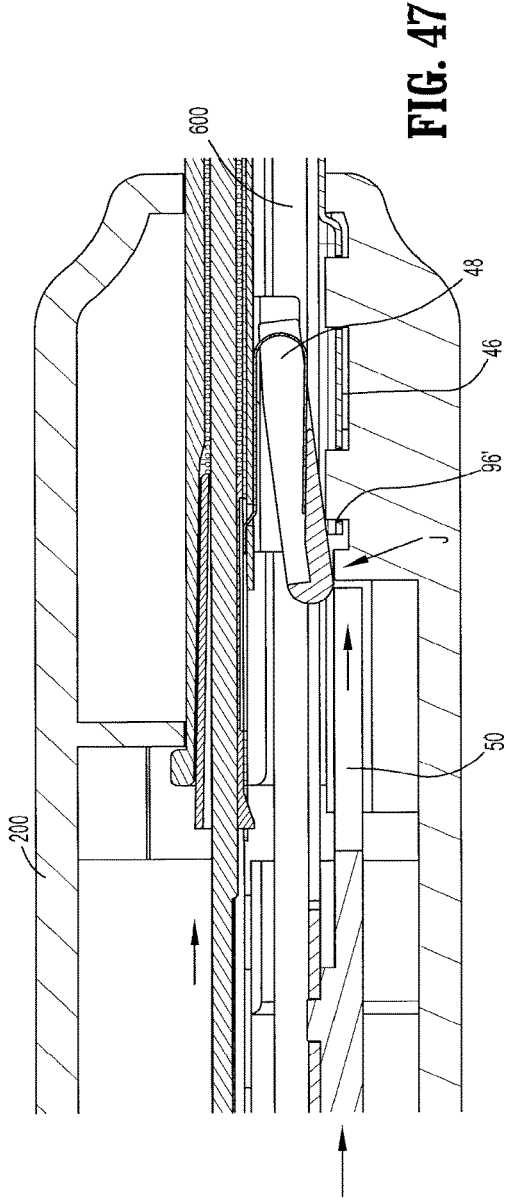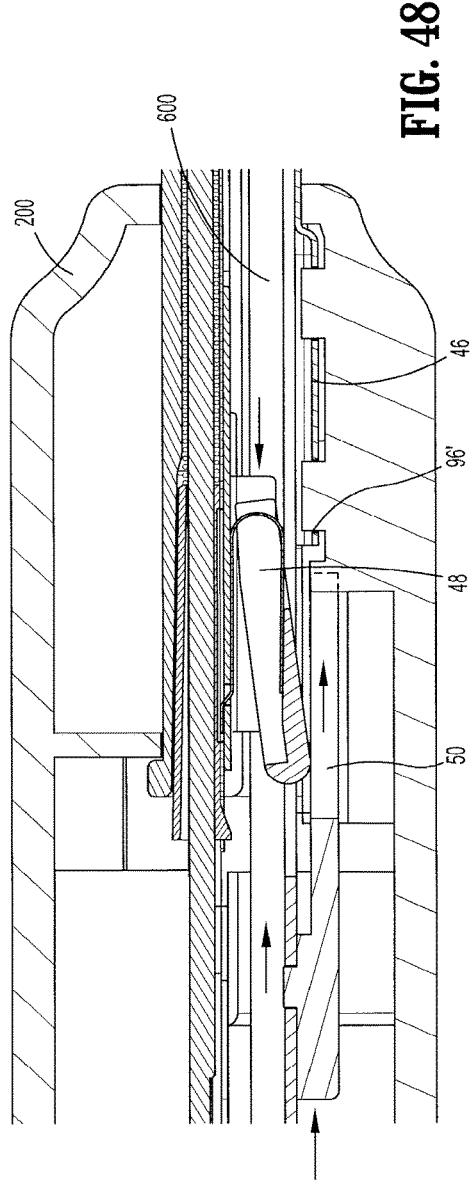

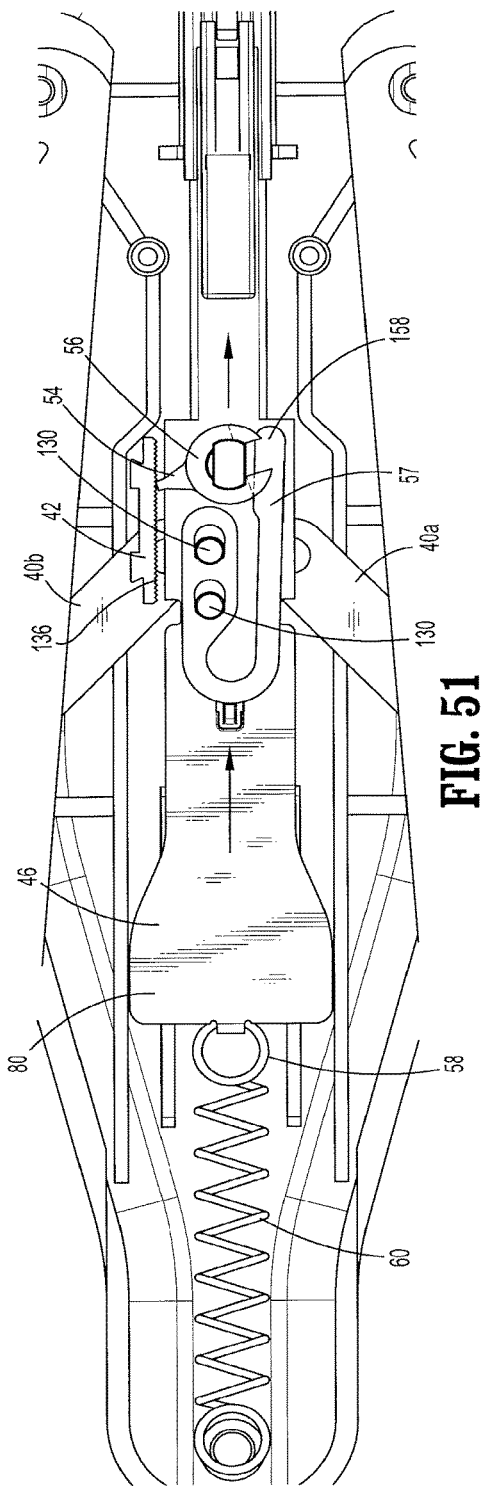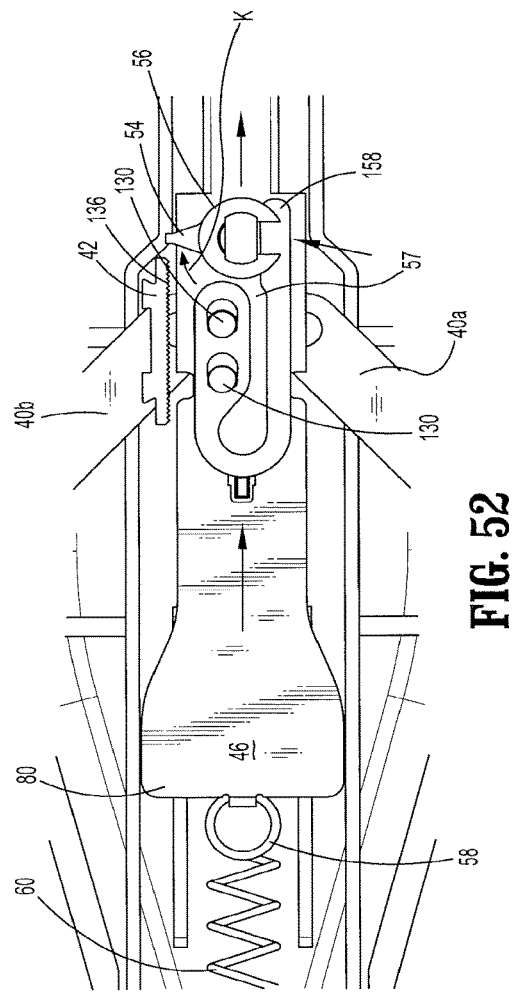
FIG. 51
FIG. 52

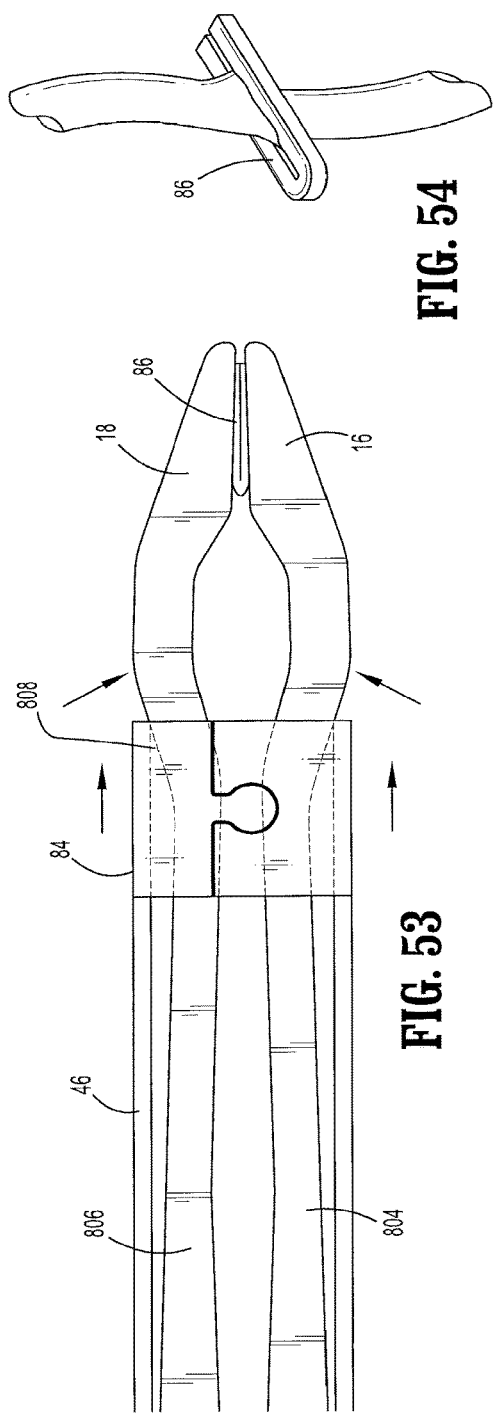
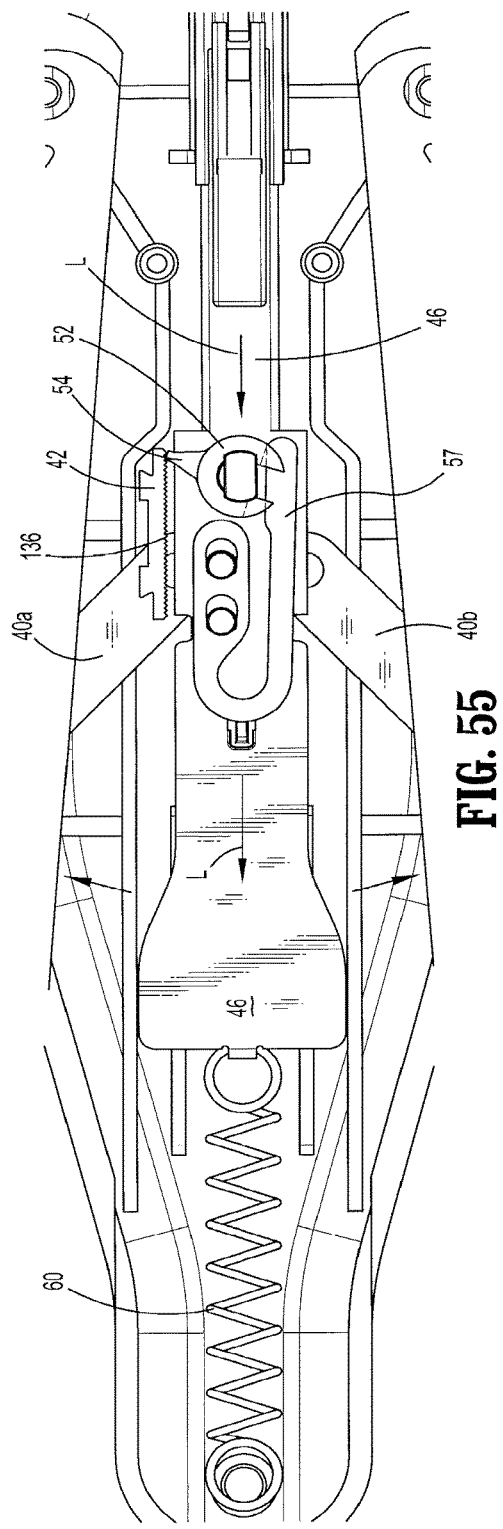

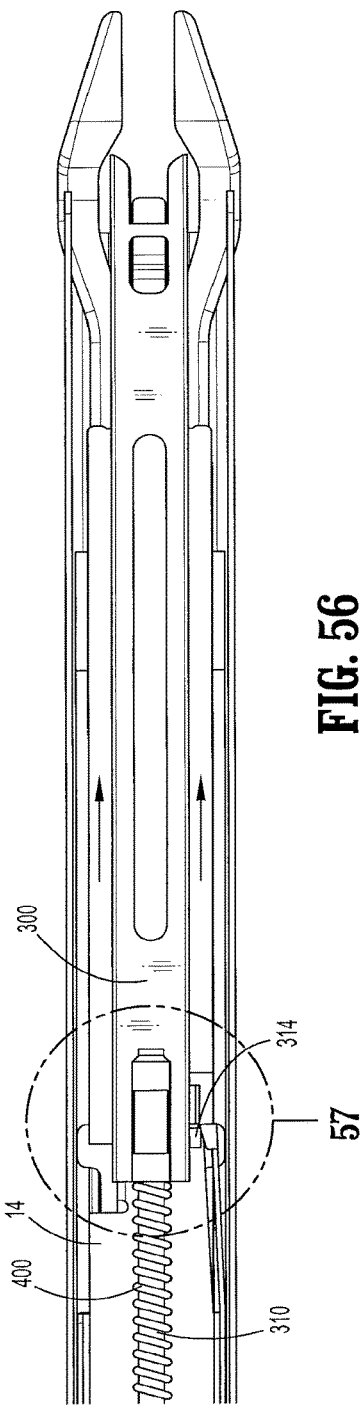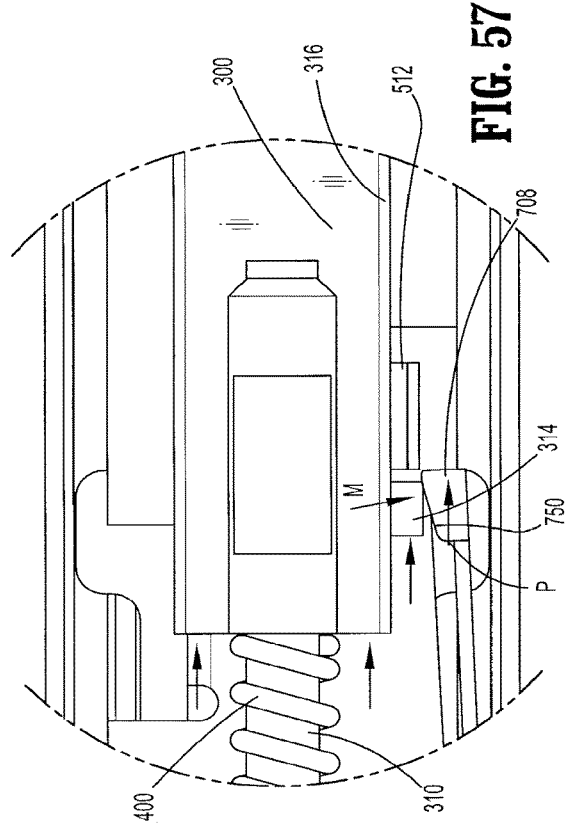

APPARATUS FOR APPLYING SURGICAL CLIPS

CROSS-REFERENCE TO RELATED APPLICATION

The present application is a Continuation Application claiming the benefit of and priority to U.S. patent application Ser. No. 14/072,010, filed on Nov. 5, 2013, now U.S. Pat. No. 9,480,477, which is a Continuation Application claiming the benefit of and priority to U.S. patent application Ser. No. 13/358,542, filed on Jan. 26, 2012, now U.S. Pat. No. 8,603,109, which is a Divisional Application claiming the benefit of and priority to U.S. patent application Ser. No. 11/872,750, filed Oct. 16, 2007, now U.S. Pat. No. 8,128,643, which claims the benefit of and priority to U.S. Provisional Application Ser. No. 60/852,143, filed on Oct. 17, 2006, the entire content of each of which is incorporated herein by reference.

BACKGROUND

1. Technical Field

This present disclosure relates generally to an apparatus for applying surgical clips to tissue. More specifically, the present disclosure relates to an apparatus for applying a series of clips to tissue seriatim.

2. Background of Related Art

Surgical procedures frequently require ligation of blood vessels, severed tissues and/or other organs to control or stop bleeding. Clip applying apparatus for quickly applying a surgical clip about tissue are known. Such clip applying apparatus include single clip applicators and multiple clip applicators. In single clip applicators, a new clip is loaded into the apparatus after application of each clip. Multiple clip applicators include a series of clips which can be sequentially applied to tissue during the course of a surgical procedure. Because surgical procedures usually require the use of a multiplicity of surgical clips, multiple clip applicators are generally preferred.

Typically, clip applying apparatus include a handle mechanism, an elongated body portion, and a clip crimping assembly, e.g., a jaw or pair of jaws. Such clip applying apparatus are configured for endoscopic or open surgical procedures. Although known clip applying apparatus for sequentially advancing individual clips have provided good results, a continuing need exists for a clip applying apparatus which is less complex and provides effective occlusion of a blood vessel.

Often some issues arise where the instrument can be manipulated while not in operation such as for loading on a surgical tray prior to surgery. This movement can result in an accidental movement and/or compression of the jaws. Other issues arise where other prior art clip applier can be fired without the surgeon aware that there are no remaining clips in the instrument. The present disclosure includes clip applier subassemblies to remedy some of these longstanding concerns in an effective manner in an instrument which is less complex.

SUMMARY

In a first embodiment of the present disclosure, there is provided an apparatus for applying surgical clips. The apparatus has a body portion housing a clip stack and a pair of jaws supported at a distal end of the body portion. The apparatus has the body portion including a clip pusher, a camming member and a clip follower. The clip pusher is movably positioned within the body portion and being operable to advance a distal-most clip from the clip stack to a position between the pair of jaws. The camming member is movably positioned within the body portion and operable to approximate the pair of jaws to deform the distal-most clip. The clip follower is positioned proximally of the clip stack and operable to urge the clip stack distally towards the pair of jaws. The body portion further includes a lockout member having a plurality of stop members. The lockout member is movable from a first position in slidable relation to the camming member to a second position interlocked with the camming member. The camming member has at least one notch, and in a second position the lockout member has at least one of the stop members being positioned to operatively engage the at least one notch. The engagement between the stop member and the notch limits distal movement of the camming member. The clip follower actuates the lockout member when the clip follower advances to a predetermined position in the clip stack.

According to another embodiment, there is provided an apparatus for applying surgical clips. The apparatus has a body portion housing a clip stack; and a pair of jaws supported at a distal end of the body portion. The body portion has a clip pusher, a camming member and a clip follower. The clip pusher is movably positioned within the body portion and operable to advance a distal-most clip from the clip stack to a position between the pair of jaws. The camming member is movably positioned within the body portion and operable to approximate the pair of jaws to deform the distal-most clip. The clip follower is positioned proximally of the clip stack and operable to urge the clip stack distally towards the pair of jaws. The body portion further includes a lockout member having a plurality of stop members. The lockout member moves from a first position in slidable relation to the camming member to a second position interlocked with the camming member. The camming member has at least one notch. In the second position, the lockout member has at least one of the stop members positioned to interface with at least one notch to limit distal movement of the camming member. The clip follower actuates the lockout member when the clip follower advances to a predetermined position in the clip stack.

The apparatus also has a latch assembly supported on the clip pusher. The latch assembly includes a pivotal latch member having a member which is movable from a first position to engage an aperture supported on the clip pusher to load a clip between the jaws to a second position. In the second position, the latch member disengages to retract the clip pusher. The camming member is operably connected to a movable handle such that movement of the at least one movable handle through an actuation stroke effects movement of the camming member from the advanced position to the retracted position.

According to yet another embodiment of the present disclosure there is provided a clip follower and a lockout for a surgical hemostatic clip applier. The clip follower comprises a body having a post configured to receive a biasing member and a distal end configured to urge a clip stack in a distal manner. The clip follower also has an indexing nub on a lateral side. The nub is adapted to actuate the lockout when the clip follower has reached a predetermined position of the clip stack.

BRIEF DESCRIPTION OF THE DRAWINGS

Various embodiments of the presently disclosed clip applying apparatus are described herein with reference to the drawings, wherein:

FIG. 1 is a perspective view of one embodiment of the presently disclosed clip applying apparatus;

FIG. 2 is an enlarged perspective view of the distal end of the clip applying apparatus shown in FIG. 1;

FIG. 6 is a perspective view of the clip applying apparatus shown in FIG. 1 with the top housing half-section removed;

FIG. 7 is an enlarged view of the distal end of the clip applier showing the jaws;

FIG. 12 is an enlarged view of a clip follower shown in FIG. 8 according to the present disclosure having a lockout member in a side;

FIG. 13 is a top view of the separator plate of the clip applying apparatus;

FIG. 14 is a bottom view of the plate of FIG. 13;

FIG. 15 is a bottom view of a cover of the clip applier showing the clip retainer spring of FIG. 8;

FIG. 16 is a perspective view of the clip applying apparatus shown in FIG. 8 with multiple subassemblies in a partially assembled state;

FIG. 17 is an enlarged view of FIG. 16 of the clip retainer spring with the clip stack, and jaws with the cover being removed;

FIG. 18 is a perspective view of the separator plate of the clip applying apparatus having a lockout engagement member of the lockout beneath the plate extending through the separator plate;

FIG. 19 is an enlarged perspective view of the follower with follower spring shown in FIG. 16;

FIG. 20 is a perspective view of a partially assembled clip applier instrument having the lockout, the jaws, and the latch assembly;

FIG. 21 is a perspective view of the latch and pusher spring connected to the separator plate;

FIG. 22 is a top perspective view of the lockout member having the legs for engagement with the cam plate and the lockout being adjacent the jaws as shown in FIG. 8;

FIG. 25 is a partially assembled perspective view of the clip applying apparatus with the jaw safety and clip pusher and lockout engagement member;

FIG. 26 is a partially assembled perspective view of the lockout having the lockout legs for engagement into the slots of the cam plate;

FIG. 27 is a side view of the assembled clip applier;

FIG. 28 is a top view of the assembled clip applier of FIG. 27;

FIG. 29 is a top view of the handle portion of the clip applying apparatus shown in FIG. 1 with the top handle cover removed to show the cam plate in an initial position and biased to an end of the handle portion and with the pawl adjacent the rack;

FIG. 30 is a cross sectional side view of the handle portion of the clip applier shown in FIG. 29 with the cam plate, the pawl and the latch along line 30-30 of FIG. 29;

FIG. 31 is a cross sectional side view of the body portion of the clip applier shown in FIG. 27 with the jaw safety, the clip retainer, the camming member and the lockout;

FIG. 32 is a top view of the distal end of the body portion shown in FIG. 31 with the clip pusher ready to advance a distal most clip between the jaws with the cover being removed;

FIG. 33 is a cross sectional side view of the lockout member in the body portion with the clip stack and lockout spring;

FIG. 34 is a top view of the body portion shown in FIG. 33 with the lockout member being shown under the separator plate and the clip stack in phantom dotted lines to show the flexible legs of the lockout;

FIG. 35 is a cross sectional side view of the proximal end of the body portion with the latch spring and latch;

FIG. 36 is a top cross-sectional view of the clip applying apparatus shown with the clip follower urging the clip stack in a distal manner;

FIG. 40 is a top view of the handle portion showing the beginning of the stroke and the triggers being squeezed;

FIG. 47 is a cross-sectional view of the latch driver, latch and latch spring with the latch being cammed up and out of engagement with the latch driver;

FIG. 48 is a cross-sectional view of the latch cammed out of engagement with the latch driver to allow the clip pusher to retract with the latch driver and the cam plate being advanced distally;

FIG. 51 is a top view of the handle portion of the clip applying apparatus shown with the pawl contacting the teeth of the rack to prevent the cam plate from being retracted until the clip is formed;

FIG. 52 is a top view of the handle portion of the clip applying apparatus shown with the pawl being past the teeth of the rack and reset at a full stroke;

FIG. 53 is a view of the cam plate closing the jaws at a full stroke;

FIG. 54 is view of the formed clip on a blood vessel with the clip applier being withdrawn;

FIG. 55 is a top view of the handle portion of the clip applying apparatus shown in FIG. 1 with the trigger being released and the cam plate commencing retraction;

FIG. 56 is a top view of the body portion with a clip follower having a member contacting an engagement member of the lockout member;

FIG. 57 is an enlarged view of detail of FIG. 56 showing the lockout member of the clip follower moving the engagement member of the lockout past a raised feature of the separator plate after a predetermined clip has been fired.

DETAILED DESCRIPTION OF THE EMBODIMENTS

Figure 3:
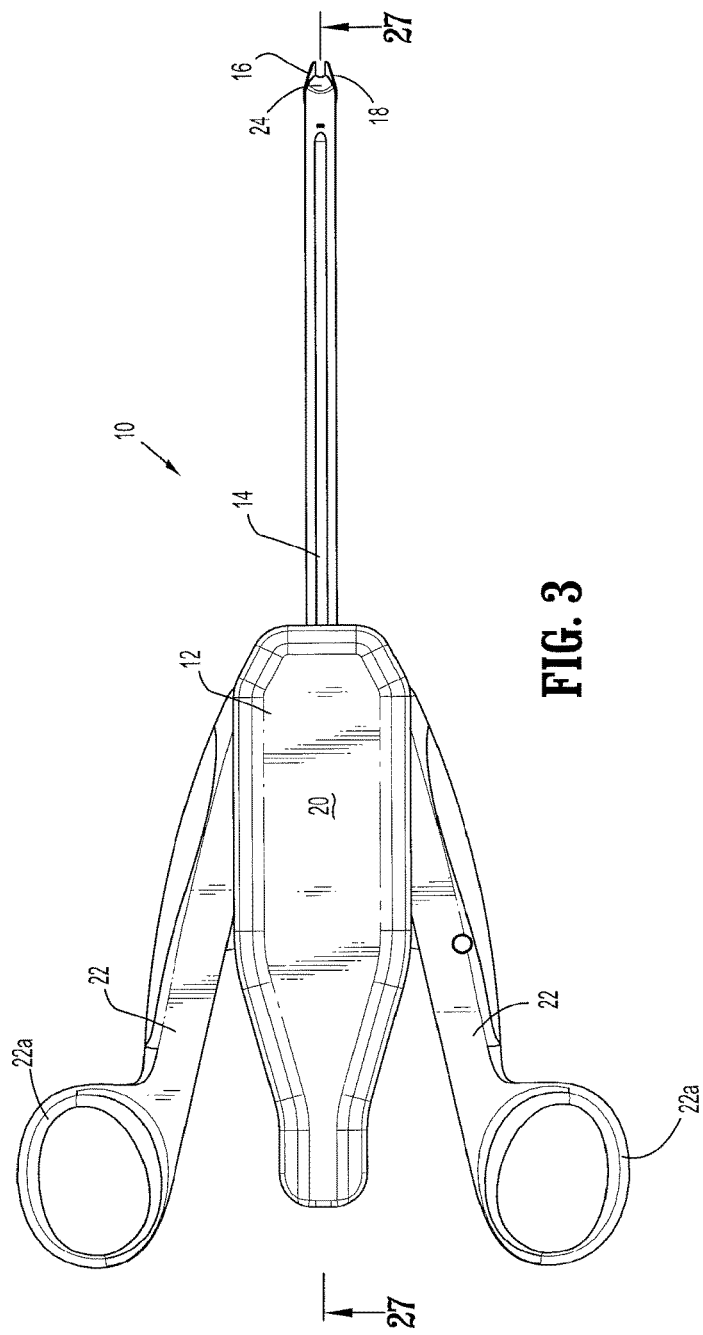
FIG. 3 is a top view of the clip applying apparatus shown in FIG. 1.
Figure 4:
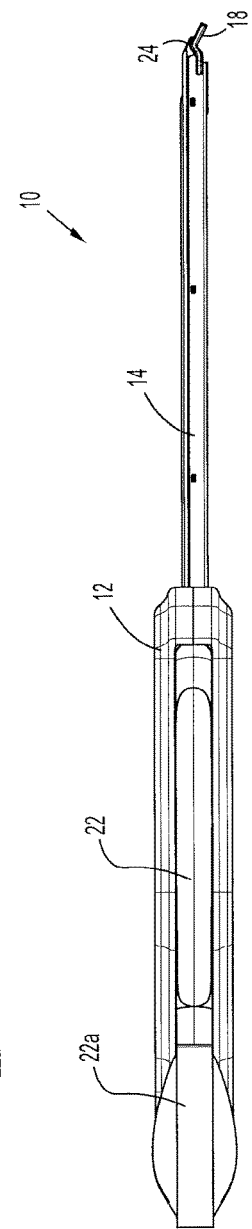
FIG. 4 is a side view of the clip applying apparatus shown in FIG. 1.

Embodiments of the presently disclosed surgical clip applier will now be described in detail with reference to the drawings wherein like reference numerals designate identical or corresponding elements in each of the several views. Throughout this description, the term "proximal" will refer to the portion of the instrument closest to the operator and the term "distal" will refer to the portion of the instrument furthest from the operator.

Referring to FIGS. 1 through 4, the presently disclosed surgical clip applier, shown generally as reference numeral 10, includes a handle portion 12, an elongated body portion 14 extending distally from handle portion 12 and first and second jaws 16 and 18. The first and the second jaws 16, 18 extend from the distal end of body portion 14. Briefly, handle portion 12 includes a handle housing 20 and a pair of movable handles or triggers 22. Each movable handle or trigger 22 includes a finger loop 22a for receiving a finger of a surgeon's hand. As can be understood from FIG. 1, the handle housing 20 with the triggers 22 can be comfortably held in a surgeon's hand and actuated without any undue strain on the surgeon's fingers or palm. The present clip applier 10 further has a smooth outer surface that is comfortable to hold. Referring now to FIG. 2, the clip applier 10 has a tissue stop 24 formed at a distal end of a cover 200 that extends above the jaws 16, 18 and prevents any tissue from entering a distal portion of the body portion 14. In one embodiment, the tissue stop 24 is made from a visually translucent or transparent material so as to allow the surgeon the ability to visually inspect an interior through the tissue stop 24 and inspect in the interior of the surgical clip applier 10. Tissue stop 24 also prevents tissue from forcing/moving a clip proximally in jaws 16, 18. Tissue stop 24 also prevents/minimizes deflection of jaws 16, 18.

Referring also to FIGS. 5 through 9, the handle housing 20 can be formed from molded housing half-sections 20a and 20b (FIG. 5) which are secured together using a screw 30. Alternately, other fastening techniques may be used to secure housing half-sections 20a and 20b together, e.g., welding, rivets, interlocking structure, adhesives, etc.

In one embodiment, the distal end of each handle 22 is pivotally secured about a pivot member 26a, 26b such that handles 22, when actuated, move in a scissor-like manner. Each pivot member 26a, 26b is positioned between recesses 28a, and 28b formed in half-sections 20a and 20b, respectively, and may be formed integrally with a respective handle 22 or, in the alternative, as a separate element from a respective handle 22.

In one exemplary embodiment, each handle 22 may have a slip resistant grip member 32 secured to an outside surface thereof and a cam channel 34 formed on an inside surface 36 thereof. Slip resistant grip member 32 can be formed from a cushioning material, adhered or connected or over molded onto each handle 22. It is also contemplated that other slip resistant materials and methods of application may be used to form grip member 32 and/or apply grip member 32 to the handles 22. Each cam channel 34 is configured to receive a pivot member 36a, 36b for connecting a pair of pivotal links 40a, 40b as will be described in more detail below.

Figure 5:
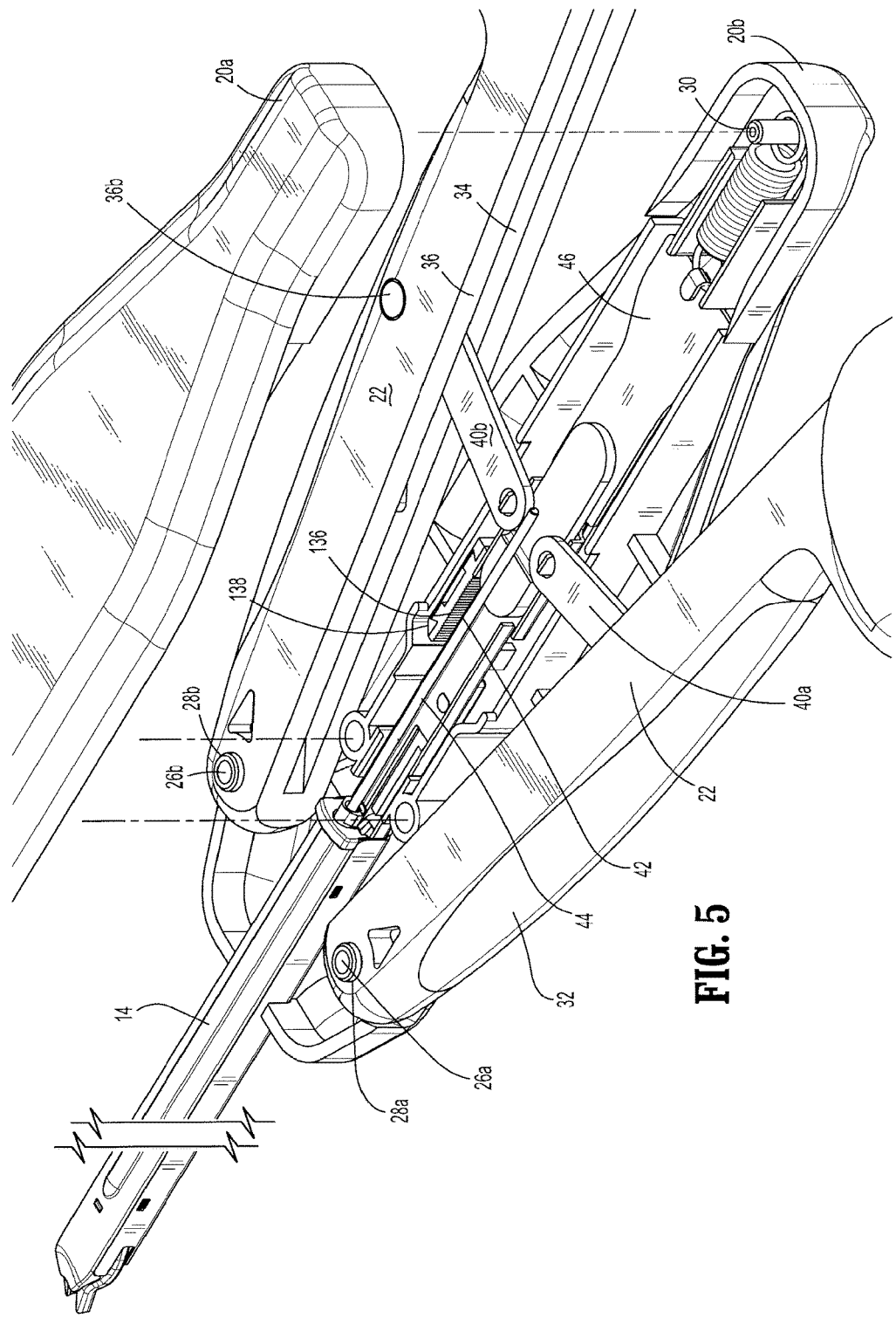
FIG. 5 is a perspective view of the proximal portion of the handle of the clip applying apparatus shown in FIG. 4 with the top housing half-section exploded.

Referring now to FIG. 5, the clip applier 10 has a rack 42 and a follower 44 that is disposed through the handle portion 12. The handle portion 12 also has a cam plate or camming member 46 shown in a proximal most section of the handle portion 12. The cam plate 46 also extends through the body portion 14 of the clip applier 10. The cam plate 46 may be a thin resilient coined member that translates the energy from the handles 22 to drive one or more internal structures of the clip applier 10 with ease and repeatability.

Referring now to FIG. 6, there is shown the opposite side of the clip applier 10 of FIG. 5 except with a half housing section 20b being removed for clarity. The clip applier 10 has a latch 48. The latch 48 is advanced distally by a latch driver 50 (see below). The latch 48 and the latch driver 50 are an assembly that translates energy to a clip pusher (not shown) and for loading the distal most clip between the jaws 16, 18. Thereafter, the latch 48 will then move proximally to withdraw the clip pusher (not shown) and permit one or more other structures to operate without any interference. The latch 48 is connected to a clip pusher 600 while latch driver 50 is connected to the cam plate 46.

The clip applier 10 further has a pawl 56 with a pawl finger 54. The pawl finger 54 is a resilient pointed member that is pivotally connected at one end to the ratchet support 52 and is free at the other end to interface with another structure. The pawl finger 54 at the free end interfaces with the rack 42 of FIG. 5. The pawl 56 is further connected in the handle portion 12 and is connected to a pawl spring 57. The pawl spring 57 is mounted to the camming member 46. The camming member 46 further has a hook 58 and is connected by a spring 60 to a proximal most section of the handle portion 12 in the handle housing 20 (FIG. 6). As can be understood, as the camming member 46 is urged distally, the spring 60 (connected to the hook 58 and the handle portion 12) will be stretched and then urge the camming member 46 to return proximally.

Referring to FIG. 7, there is shown a close up view of the first and the second jaws 16, 18. The first and the second jaws 16, 18 are stationary and do not move proximally or distally. Instead, the first and the second jaws 16, 18 move toward one another in order to compress a clip being disposed between the first and the second jaws 16, 18. The body portion 14 includes a pair of distally located cutouts 62 (only one of which can be seen in FIG. 7). The cutouts 62 are configured to slidably receive the jaws 16 and 18. The cutouts 62 are generally rectangular shaped and dimensioned to confine jaws 16 and 18 to prevent misalignment of the jaws 16, 18 during actuation of clip applier 10. The proximal end of the body portion 14 includes a pair of transversely extending wings 64 of the jaws 16, 18 integrally formed therewith, which are dimensioned to be received within cutouts 62. Jaws 14 and 16 are manufactured as a single unitary component, however, it is envisioned that jaws 14 and 16 may be manufactured as two separate components.

Figure 8:
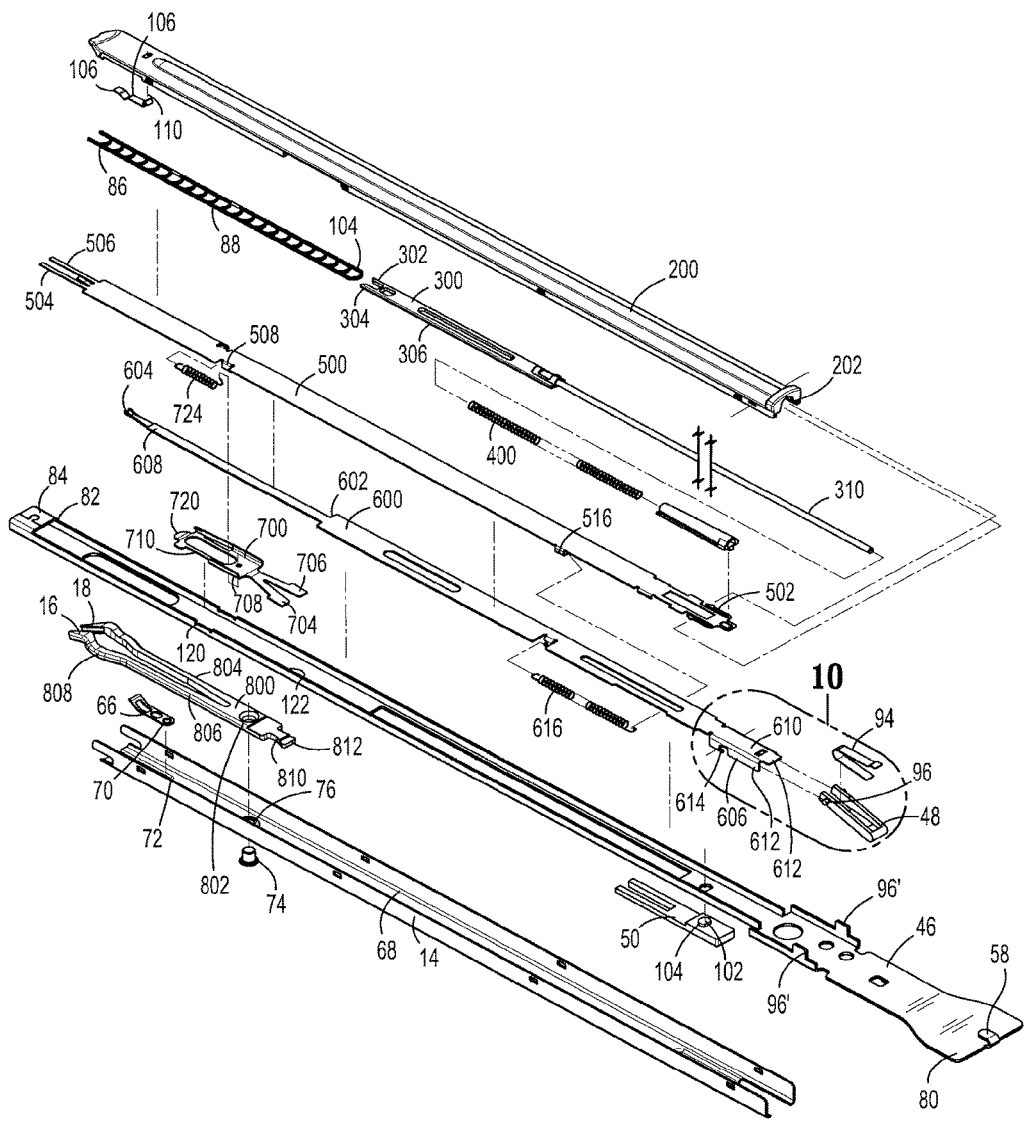
FIG. 8 is an exploded view of the body portion of the clip applying apparatus shown in FIG. 1.

Referring to an exploded view of the clip applier 10, as shown in FIG. 8, the clip applier 10 also has a jaw locking member or plate 66. The jaw locking plate 66 is secured to the housing body 14 and in a channel 68 of the housing body 14. The jaw locking plate 66 includes an opening 70. The opening 70 is sized to receive a projection 72 formed on or in the housing body 14 to secure the jaw locking plate 66 to the clip applier 10. In one embodiment, the jaw locking plate 66 may be connected to the housing body 14 by a screw with a washer to prevent any body fluids from entering the channel 68 and that could interfere with the operation of one or more subassemblies thereof.

FIG. 8 shows an exploded view of a number of components of the surgical clip applier 10. The surgical clip applier 10 has a cover 200, a follower 300, a follower spring 400, a separator plate 500, a clip pusher 600, a lockout or lockout member 700, a jaw body 800, the latch driver 50, the camming member 46, and the channel 68 of the housing body 14. The components here are shown as exploded, however, the components fit in the assembled state in the channel 68, and the cover 200 connects with the housing body 14 by a snap fitting or another suitable connector. Optionally, when the housing body 14 is connected to the cover 200, a poly vinyl chloride or a Mylar™ may wrap the cover 200 and housing body 14 having a thickness.

As can be understood from the drawings, referring first to the jaw body 800 shown between the channel 68 of the housing body 14 and the camming member 46, the jaw body 800 is stationary. The jaw body 800 and includes jaws 16 and 18, a proximal mounting portion 802 and a pair of spaced distally extending legs 804, 806.

The jaw 16 is connected to a distal end of the leg 806. The other jaw 18 is also connected to another distal end of the leg 804. An outer cam surface 808 is formed on an outer surface of each jaw 16 and 18. As can be understood the jaws 16, 18 are intended to be closed by another member traversing and contacting on the outer cam surface 808 of the jaws 16, 18 to close and compress the jaws 16, 18 and a clip being disposed between the jaws 16, 18. The cam surfaces 808 are positioned to be engaged by an engagement member 84 connected to the camming member 46 shown immediately above the jaw body 800.

The jaw body 800 is mounted within the channel 68 of the housing body 14 using a member 74 such as a bolt or fastener. The fastener 74 extends through an opening 76 in the channel 68 of the housing body 14.

The camming member 46 shown immediately above the jaw body 800 in FIG. 8 as a rectilinear structure that extends through the housing body 14 and into the handle housing 20 as shown in FIG. 5. The camming member 46 has a proximal end 80 that has the hook 58 as shown in FIG. 5. The camming member 46 also has a distal end 82. The camming member 46 is supported in the channel 68 of the housing body 14. The distal end 82 has the engagement member 84 that although is shown as being apart from the jaw body 800, the engagement member 84 rides up on the outer camming surface 808 when assembled. The engagement member 84 is also a rectilinear shape and is sized to interface with the camming surfaces 808 of the jaw body 800, however alternatively, the camming member 46 may have an interlocking jaw closing structure that rides up along a camming surface that is on a top of the jaw body 800 such as disclosed in U.S. Provisional Patent Application Ser. No. 60/617,104 filed on Oct. 8, 2004; U.S. Provisional Patent Application Ser. No. 60/617,016 filed on Oct. 8, 2004; and U.S. Utility patent application Ser. No. 11/245,523 filed Oct. 7, 2005, now U.S. Pat. No. 7,637,917, which are all herein incorporated by reference in their entirety.

The camming member 46 is slidably supported within channel 68 of the housing body 14. The engagement member 84 is positioned about the legs of jaw body 804, 806 in an initial unfired position. The engagement member 84 can have a substantially rectangular configuration and is formed by a one piece member that is wrapped around the distal end 82 and has an interlocking portion that secures the engagement member 84 to the camming member 46. Alternatively, another configuration is contemplated such as a square, curved or a "C" shaped configuration, or the camming member 46 and the engagement member 84 may be formed from one molded, stamped or coined piece. Various configurations are possible and within the scope of the present disclosure, and the surgical clip applier 10 may be made with any such camming member 46. Various configurations are possible and within the scope of the present disclosure.

Handles 22 of handle portion 12 shown in FIG. 5 are operable to move camming member 46 between a retracted position and an advanced position along the channel 68 of the housing body 14. In the retracted position of camming member 46, the engagement member 84 is positioned about legs 804, 806 of the jaw body 800 at a location proximal of the outer cam surface 808. In the advanced position of camming member 46, the engagement member 84 advanced distally and is positioned about the jaws 16 and 18 past the outer camming surface 808 or in abutting relation to the outer cam surfaces 808.

Referring still to FIG. 8, above the camming member 46 is the clip pusher 600 for advancing a single surgical hemostatic clip between the jaws 16, 18. The clip pusher 600 has an elongated body 602, a distal finger 604, and a proximal latch assembly mount 606 opposite the distal finger 604. The distal finger 604 is on a distal end 608 of the clip pusher 600. The distal finger 604 has an elongated semi-circular shape and is positioned to engage distal-most clip 86 of the stack of clips 88 when the clip pusher 600 is moved from a retracted position to an advanced position. In this manner, the distal finger 604 will advance only the distal most clip 86 for compression between the jaws 16, 18. Referring to an opposite or proximal end 610 of the clip pusher 600 is the latch assembly mount 606. The latch assembly mount 606 has a pair of spaced, vertical brackets 612. The vertical brackets 612 have an opening 614. The opening 614 is sized to receive pivot pins 96 of the latch 48.

The pusher latch assembly generally 90 has the latch 48, a latch spring 94, and pivot pins 96 that extend on the outermost sides of the latch 48. Alternatively, the pusher latch assembly 90 may have one pin 96 that extends through the latch member 48, or yet another connector to translate energy from the handles 22 to the clip pusher 600. The latch member 48 has the pins 96 pivotally secured at a distal end in the opening 614 of the latch assembly mount 606 of the clip pusher 600. The opening 614 is a semicircular shaped opening on a bottom side of the latch assembly mount 606 that is formed in the brackets 612 that are generally orthogonal relative to one another.

The latch spring 94 is positioned between the proximal end of clip pusher 600 and the latch 48. The latch spring 94 urges the latch 48 away from clip pusher 600. Accordingly, the pins 96 of the latch 48 engage the opening 610 of the clip pusher 600 when the camming member 46 moves to the advanced position.

The latch 48 is pivotal against the urging of latch spring 94 and towards the proximal end 610 of clip pusher 600 to move latch 48 out of engagement with the opening 614 as will be discussed in further detail below.

Referring still to FIG. 8, the clip applier 10 also has the separator plate 500. The separator plate 500 is fixedly supported between housing body 14 and a housing cover 200. The separator plate 500 has a series of projections 502. The projections 502 are dispersed about the separator plate 500 and the projections 502 are received in recesses 202 formed in housing cover 200. In this manner, the separator plate 500 is secured to the housing cover 200, and is fixably supported in the clip applier 10 to be stationary relative to the other components. Moreover, other components of the clip applier 10 can be connected to the stationary separator plate 500 and move relative to the plate 500 without disturbing an orientation of the separator plate 500.

Referring now to the distal end of separator plate 500, the separator plate has a pair of spaced spring fingers 504, 506. The distal most fingers 504, 506 are positioned to guide the distal-most clip 86 of clip stack 88 in between the jaws 16 and 18. One should appreciate that at no time before the distal most clip 86 is positioned between the jaws 16, 18, the geometry of the clip is undisturbed and that the clip 86 is in no way deformed, knocked, nicked or compressed prior to entering the jaws 16, 18 as this may disturb the manner in which the clip 86 is compressed around a vessel. The clip applier 10 advantageously maintains the geometry of the clip 86 prior to compression thereof.

Referring now to FIG. 14, there separator plate 500 has a first hook 508 that is on a first bottom side 510 of the separator plate 500. The first hook 508 engages with biasing device for the lockout 700. The separator plate 500 also has a second hook 516. The second hook 516 connects with another biasing device for the clip pusher 600, or a pusher spring 616 shown in FIG. 8. The pusher spring 616 connects with the separator plate 500 by hooking on the second hook 516. The coiled pusher spring 616 is tensioned. The coiled pusher spring 616 urges the clip pusher 600 to its retracted position once the clip pusher 600 is advanced distally.

Referring back to FIG. 13, the separator plate 500 also has a lockout member 512, which will be discussed in detail below. The lockout member 512 is an orthogonal shaped member that extends perpendicular to a normal face of a top side 514 of the separator plate 500. The lockout member 512 biases the lockout 700 until such time as the clip follower 300 advances a portion of the lockout 700 past the member 512.

Referring again to FIG. 8, when the handles 22 shown in FIGS. 1 through 4 are operated to move camming member 46 from its retracted position to its advanced position, the abutment member 96' engages the latch 48. The abutment member 96' is a raised feature on the camming member 46 that urges the latch member 48 and the clip pusher 600 in a distal direction or toward a distal most advanced position against the urging of pusher spring 616. As discussed above, the pusher spring 616 is connected to the second hook 516 of the separator plate 500 shown in FIG. 13. As clip pusher 600 moves distally with camming member 46, a distal finger 604 of the clip pusher 600 engages distal-most clip 86 of the clip stack 88. In this manner, the distal most clip 86 is advanced by the finger 604 between jaws 16 and 18.

Referring still to FIG. 8, a latch driver 50 is supported in the channel 68 between the housing body 14 and the housing cover 200. The latch driver 50 is a "U" shaped member having an aperture 102 being disposed therethrough. The aperture 102 has a pin 104. The pin 104 or fastener may be any fastener in the art that is disposed through the aperture 102 and connects the latch driver 50 with the camming member 46.

The latch driver 50 is positioned in cam channel 68 at a position to engage the distal end 80 of latch member 48. The latch driver 50 slides and disengages latch member 48 from the abutment member 96' when distal-most clip 86 has been fully advanced into jaws 16 and 18.

When the latch driver 50 is disengaged from abutment member 96', the pusher spring 616 returns the clip pusher 600 to its retracted position. Although latch driver 50 is illustrated as having a "U" shape other configurations are envisioned.

Referring to FIG. 8, the clip stack 88 may have any number of surgical hemostatic clips in the stack 88 for applying the clips to body tissues in a repeated fashion. The stack 88 is slidably supported on top side 514 of the separator plate 500. The clip follower 300 is positioned behind the proximal-most clip 104 of the array of the clips in the clip stack 88. The clip follower 300 includes a pair of distally extending arms 302, 304, and a body portion 306. The distal end 308 of each of the clip follower arms 302, 304 is configured to engage an apex or another portion of the proximal-most clip 104.

The clip follower 300 also has a top surface 308. Referring now to FIGS. 8 and 12, the top surface 308 of the clip follower 300 has a member or post 310. The member 310 is generally cylindrical shaped and has the spring 400 in coaxially alignment with the member 310 in order to bias the member 310 distally and to advance a distal most clip 86 between the jaws 16, 18 by applying a force to the arms 302, 304 which apply the force to the stack 88. The clip follower 300 has an advantageous lockout tab or nub 314, best shown in FIG. 12.

The lockout tab 314 is a rectilinear shaped member that extends from a lateral proximal side 316 of the clip follower 300. The lockout tab 314 is positioned to engage another or second member of the clip applier 10 that is disposed on a lockout 700 and will be discussed in detail further to lockout the clip applier 10 when the clip applier 10 has no remaining clips or has few clips left in the stack 88 to prevent the clip applier 10 from being actuated without available clips for occlusion. The lockout tab 314 acts as an indexer and travels distally each time the clip applier 10 is fired and the number of clips from the clip stack 88 are applied to tissue for occlusion. At a certain line of demarcation in order to prevent the clip applier 10 from further operating and dry firing the clip applier, the clip applier 10 will lock and not fire when the handles 22 are compressed. This provides the surgeon with a tactile feedback that the handles 22 can no longer be compressed. Thus, the lockout tab 314 is positioned to travel in the housing body 14 and is movable with clip follower 300 as clip follower 300 is advanced to move clip stack 88 distally within elongated body portion 14.

Referring still to FIG. 8, the clip applier 10 has a clip retainer spring 106. The clip retainer spring 106 has a curved clip retainer member 108 and a fastener 110. The fastener 110 is connected through the clip retainer spring 106 and is connected to the housing cover 200 of the clip applier 10. The clip retainer spring 106 is further connected at a distal end of the clip applier 10 and will be discussed further herein.

A jaw locking member 66, e.g., plate (FIG. 8) is also provided and is shown above the body portion 14 and the jaw body 800 in an exploded fashion. The jaw locking member or jaw safety 66 is secured to the housing body 14 and in the channel 68 of the housing body 14. The jaw locking plate 66 has one or a number of openings 70. The openings 70 of the jaw locking plate 66 are dimensioned to receive the projection 72 (FIG. 25) formed on the housing body 14 to secure the jaw locking plate 66 to the housing body 14. The jaw locking plate 66 or safety has a resilient and flexible arm 116 on a distal end 118 which is positioned between the legs 16, 18 of the jaw body 800 to prevent the jaws 16, 18 from being closed inadvertently during positioning of clip applier 10 at a surgical site. Again, the present clip applier 10 controls the jaws 16, 18 and separates the jaws 16, 18 to prevent the jaws 16, 18 from any premature compression, knocking or altering of the clip 86 by the jaws 16, 18 prior to the clip 86 being compressed and applied to the surgical site for occlusion.

Referring now to FIGS. 25 and 26 (with the clip pusher 600 being removed in FIG. 26 for illustration purposes), when the camming member 46 is moved to its advanced position, the distal end 82 of the camming member 46 moves the engagement member 84 of the camming member 46. This movement (of the engagement member 84) is indicative that the surgeon has squeezed the handles 22 of FIG. 5 to almost a full stroke, and is indicative that the surgeon now wishes to apply the clip 86 for occlusion. This movement (of the engagement 84) deflects the arm 116 of the jaw locking member 66 in a downward manner to move the arm 116 of the jaw locking member 66 from between the jaws 16, 18 to a position out of way of the jaws 16, 18. Thus, the jaw locking member 66 can deflect to allow for the closure of jaws 16, 18 (FIGS. 25 and 26). Alternately, the jaw locking member 66 need not be in the form of a rectilinear flat plate but rather other configurations are envisioned, e.g., cylindrical or another cantilevered configuration positionable between jaws 16, 18 to prevent closure of the jaws 16, 18. Any cantilevered shaped jaw locking member 66 is possible and within the scope of the present disclosure.

Referring to FIGS. 8 and 22, a lockout member 700 is positioned above the camming member 46 in the channel 68 of the housing body 14. The lockout member 700 has a central body portion 702, a pair of flexible legs 704, 706 and a proximally extending lockout engagement member 708. The lockout engagement member 708 is a rectilinear member that extends from a bottom surface 710 of the lockout member 700.

The central body portion 702 also includes an aperture 712 in a centermost portion 714 of the central body portion 702. The lockout 700 has legs 704, 706 extending an end of the lockout central body portion 702. The legs 704, 706 engage with a notch 120 formed in the camming member 46 shown in FIG. 8. Further the separator plate 500 shown above has the first hook 508 (FIG. 22). The first hook 508 connects a lockout spring 724 (shown in FIG. 8) and the spring aperture 712 of the lockout member 700. The lockout spring 724 biases the lockout member 700 relative to the stationary separator plate 500.

The separator plate 500 releasably retains lockout member 700 at a fixed position in relation to the separator plate 500 until an external force is applied to the lockout engagement member 708 by the clip follower 300. Simply stated, the lockout tab 314 (FIG. 12) of the clip follower 300 will move the lockout engagement member 708 as will be discussed in detail below to lockout the clip applier 10.

Referring now to FIGS. 20 and 22, the lockout 700 also has the first and the second proximally located flexible legs 704, 706. Each of the flexible legs 704, 706 of the lockout member 700 has a radial projection or edge 718. The legs 704, 706 are positioned within the confines or the sidewalls of the cam member 46 and are biased inwardly a predetermined amount by sidewalls 122 (FIG. 8).

FIG. 8 shows the notch 120 formed in the opposite sides of the sidewalls 122 of the camming member 46. Accordingly, when the lockout member 700 is moved so that the legs 704, 706 are in direct alignment with the notch 120, the legs 704, 706 of the lockout member 700 will move not being constrained by the sidewalls 122 of the camming member 46. The legs 704, 706 will spring in a direction outwardly and be free from the constraint of the sidewalls 122. The legs 704, 706 of the lockout member 700 move the radial projections or edge 718 of the legs 704 into the notch 120. When the legs 704, 706 are positioned within the notch 120, the lockout member 700 is fixedly secured to the camming member 46.

As discussed above, the follower 300 is urged distally by the biasing member or follower spring 400. The follower spring 400 urges the clip stack 88 distally along separator plate 500. Each clip is advanced between the jaws 16, 18, because the clip follower 300 moves further distally within elongated body 14 due to the bias of the follower spring 400.

As the proximal-most clip 104 or a predetermined clip prior to the proximal most clip (such as with one, two or three clips remaining in the stack 88) is advanced in between the jaws 16, 18 a lockout tab 314 of follower 300 engages a lockout engagement member 708 of the lockout 700 and effects distal movement of lockout 700 in relation to the camming member 46, such that after proximal-most clip 104 is crimped between the jaws 16, 18 and the camming member 46 is returned to its retracted position, the radial projection or edge 718 of the legs 704, 706 of the lockout 700 align with the notch 120 in the camming member 46 to fixedly secure the lockout 700 to the camming member 46 and thus prevent further movement of the camming member 46 (FIG. 26).

Referring now to the jaw body 800 (shown between the housing body 14 and the camming member 46 in FIG. 8), the jaw body 800 has a stop member 810 secured to a proximal end 812 of the jaw body 800. Alternately, other stop member configurations are envisioned so as to prevent any movement of lockout 700 as a portion of the lockout 700 can engage the stop member 810 to prevent the camming member 46 from moving distally. This also prevents contact with the outer cam surface 808 of the jaw body 800.

The distal end of lockout 700 includes a tab 720. The tab 720 is a curved structure that is in a distal side of the lockout 700. The tab 720 curves slightly downwardly. The tab 720 contacts the stop member 810 that is formed in a stepped down surface in the proximal side 812 of the jaw body 800. As discussed above, after the proximal-most clip 104 has been applied to tissue, the lockout 700 is fixedly secured to the camming member 46. The engagement between the lockout tab 720 and another stop member 810 prevents distal advancement of the camming member 46.

As will be discussed below, since the camming member 46 is connected via links 40a, 40b to handles 22 (FIG. 1), the engagement between the lockout 700 and the camming member 46 prevents actuation of the handles 22. In fact, if the surgeon attempts to compress the handles 22, the handles 22 will provide a stiff resistance to the compression and thus, indicate by a tactile feedback to a surgeon that the clip applier clip stack 88 has been depleted.

Figure 9:
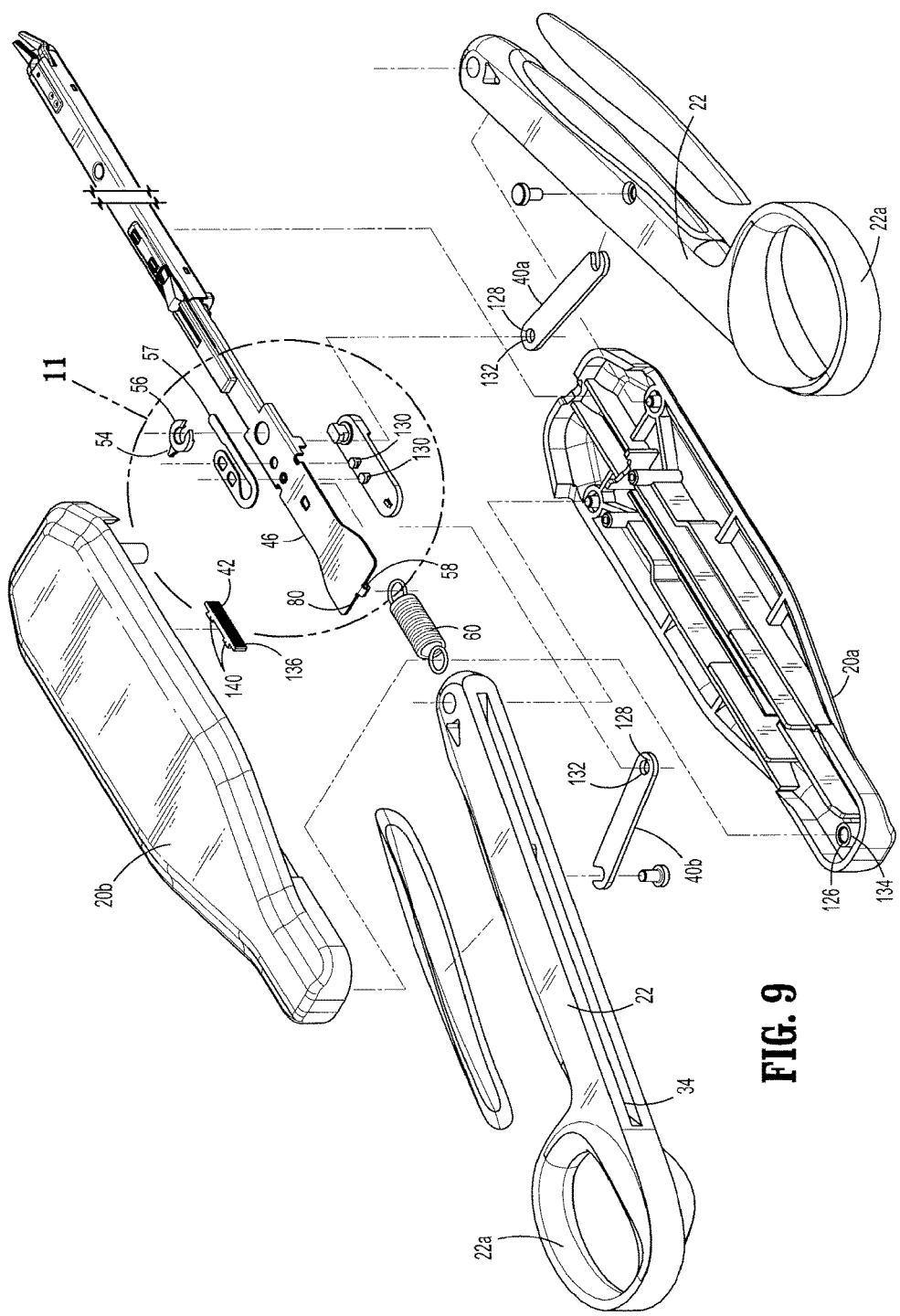
FIG. 9 is an exploded view of the handle section showing the pawl, rack and pawl spring with the triggers and links.
Figure 10:
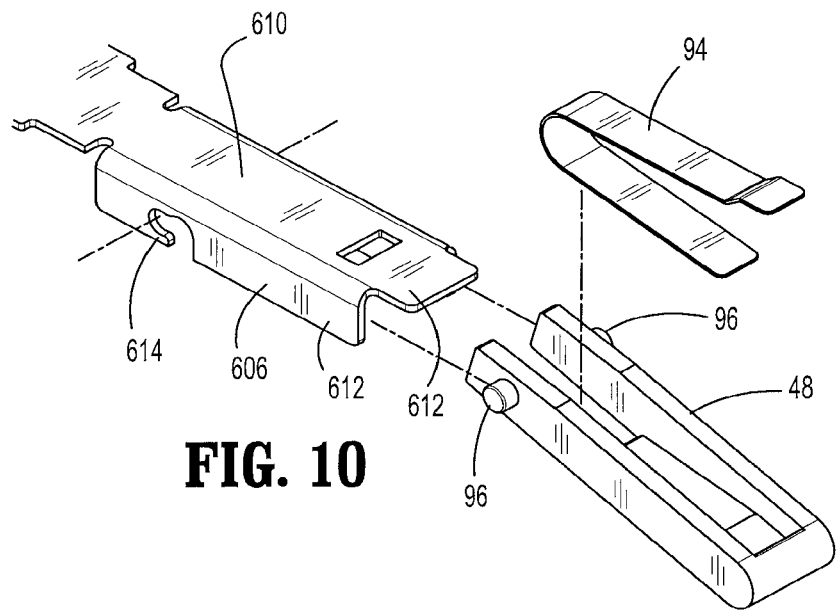
FIG. 10 is an exploded view of the latch, latch spring and proximal end of the clip pusher.

Referring to FIG. 9, the handle portion 12 has the camming member 46 having the proximal end 80. The proximal end 80 of the camming member 46 has the hook 58. Hook 58 connects to the spring 60 that is connected to the handle housing 20 at a proximal most location 128 of the handle housing 20.

The clip applier 10 has links 40a and 40b of a linkage assembly which connects handles 22 to the proximal end 80 of the camming member 46. The proximal end 128 of the links 40a, 40b are pivotally secured to the proximal end 80 of the camming member 46 respectively, by pivot members 130.

The links 40a, 40b are connected to the camming member 46 by the pivot members 130 and links 40a, 40b are pivotally mounted between bores 132 formed in each of the links 40a, 40b (FIG. 5). The links 40a, 40b are received within a respective cam channel 34 formed in a respective handle 22. When handles 22 are actuated, i.e., moved towards handle housing 20a, 20b, the links 40a, 40b are caused to move through cam channels 34 such that the links 40a, 40b are moved from a first position towards a second position (FIGS. 51 and 52).

Movement of links 40a, 40b toward the second position moves the distal ends 132 of links 40a, 40b distally within housing 20. As discussed above, the distal ends 132 of links 40a, 40b is axially fixed to the proximal end 80 of the camming member 46 by the pivot members 130.

As such, when handles 22 are actuated, camming member 46 is directly driven and moved distally. The spring 60 is positioned about the proximal end 80 of the camming member 46 and abuts a spring stop 134 supported within in proximal end 126 of the housing 20 to urge the camming member 46 to its retracted position. As mentioned, a screw 30 is disposed through the stop 34.

Referring still to FIG. 9, the handle portion 12 includes an anti-reverse ratchet mechanism which includes a pawl 56, a rack 42 and a pawl biasing member or pawl spring 57. The rack 42 includes a series of teeth 136 and is supported within a recess 138 formed in housing half-section 20b shown in FIG. 5. In one embodiment, recess 138 is dovetail shaped and the backside of rack 42 has a dovetail shape projection 140 which is slidably received within recess 138 to secure rack 42 within housing 20b. Alternately, other fastening techniques can be used to secure rack 42 within housing 20b, e.g., adhesives, pins, welding, etc.

Figure 11:
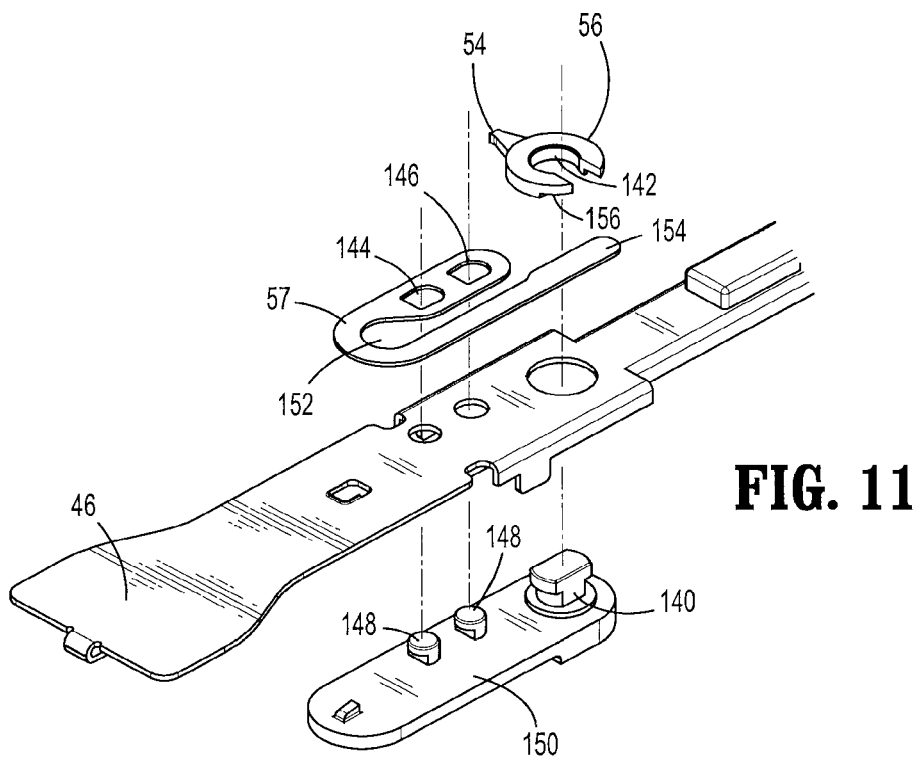
FIG. 11 is an exploded view of the cam plate of the clip applying apparatus with a pawl spring and pawl of FIG. 10.

Referring now to FIG. 11, the pawl 56 has a generally "C" shaped configuration with an arc having a finger 54 extending therefrom and a bore 142 dimensioned to receive pivot member 140 such that the pawl 56 is rotatably mounted to camming member 46 and the links 40a, 40b about pivot member 140. The pawl spring 57 includes a pair of mounting holes 144, 146 for securing protrusions 148 from the plate extension 150 through the camming member 46 (FIG. 11) of the clip applier 10. The pawl biasing member 57 also includes a semi-circular cutout 152 which is positioned to be clipped partially about pivot member 140, and has a cantilever or spring arm 154 which is positioned within a side 156 formed in a side of pawl 56.

Pawl finger 54 is resilient and provides a biasing force to urge pawl 56 to a position in which pawl finger 54 is substantially perpendicular the arm 154 and generally to the longitudinal axis of the camming member 46. The pawl finger 54 is positioned to engage teeth 136 of the rack 42 (FIG. 5) and to retain the camming member 46 at partially advanced positions during actuation of clip applier 10 against the bias of spring 60 which urges the camming member 46 to its retracted position. The anti-reverse ratchet mechanism of the pawl 56 prevents retraction of the camming member 46 after the handles 22 have been partially actuated and until the clip applier 10 has been fully actuated.

Referring now to FIG. 15, there is shown a bottom view of the cover 200 with the tissue stop 24 extending from a distal side. Beneath the cover 200 or shown on a top side of the cover given that the cover 200 is inverted for illustration purposes, there is shown a view of the clip retainer spring 106 connected to the cover. The clip retainer spring 106 has a curved portion 108 that extends opposite the housing 14. The curved portion 108 holds the distal most clip 86 of the clip stack 88 until such time as the clip pusher 300 advances the distal most clip 86 past the curved portion 106 and between the jaws 16, 18.

FIG. 16 shows an assembled view of clip applier 10 with the clip stack 88, the jaws 16, and 18, the camming member 46, the clip retainer spring 106 and the clip follower 300.

Referring now to FIG. 17, there is shown a distal exploded view of the clip retainer spring 106 with the cover 200 removed for illustration purposes. The clip retainer spring 106 has the curved portion 108 that extends opposite the housing 14. The curved portion 108 deflects a predetermined amount to hold the distal most clip 86 of the clip stack 88 until clip pusher 300 advances the distal most clip 86 past the curved portion 106 and between the jaws 16, 18.

Referring now to FIG. 18, there is shown an exploded view of the clip channel 68 having the row of clips or stack 88 being disposed in the channel 68 and biased by the clip follower 300. As can be understood from the figures, the clip stack 88 is simply supported on the separator plate 500 as shown in FIG. 8. Alternatively, the clip applier 10 may be formed with a channel housing (not shown) that is disposed on the separator plate 500, for further retaining the clip stack therein. Referring to the enlarged area of detail shown as circle 24 of FIG. 18 best shown as FIG. 24, the lockout 700 has the lockout engagement member 708 that extends in an upward direction through the separator plate 500 and for simply contacting with the lockout member 512 on the separator plate 500 to initially limit the distal movement of the lockout member 700. In this manner, the lockout 700 allows for operation of the clip applier 10 as there are a sufficient number of clips in the stack 88 as determined by the lockout tab 314 of clip follower 300 being proximal of the lockout engagement member 708.

FIG. 19 shows the clip follower 300 in an exploded perspective view. The clip follower 300 is biased by a suitable clip follower spring 400. The spring 400 is a helical compression spring that is disposed to surround and connect to the proximal end or member 310 of the clip follower 300. In this manner, the clip follower 300 is biased and advances each of the clips of the stack 88 in a distal most direction for loading between the jaws 16, 18 as shown.

FIG. 21 shows the latch 48 on a bottom side thereof. The latch 48 is connected to the separator plate 500 by the pusher spring 616 that is connected to hook 516 on the opposite side relative to the latch 48. As can be understood from the drawings, the latch 48 is biased by the latch spring 94 that is connected to the stationary plate 500. Referring now to FIG. 22, there is shown the lockout member 700. As discussed above, the lockout member 700 has a pair of legs 704, 706. Each of the legs 704, 706 move and traverse into respective notch 120 formed in the sidewalls of the camming member 46. The lockout member 700 further has the spring aperture 712. The lockout spring 724 is disposed in the aperture 712 to bias the lockout member 700 relative to the stationary separator plate 500. The opposite distal side of the spring 724 is connected to an interior first hook 508 as shown.

Figure 24:
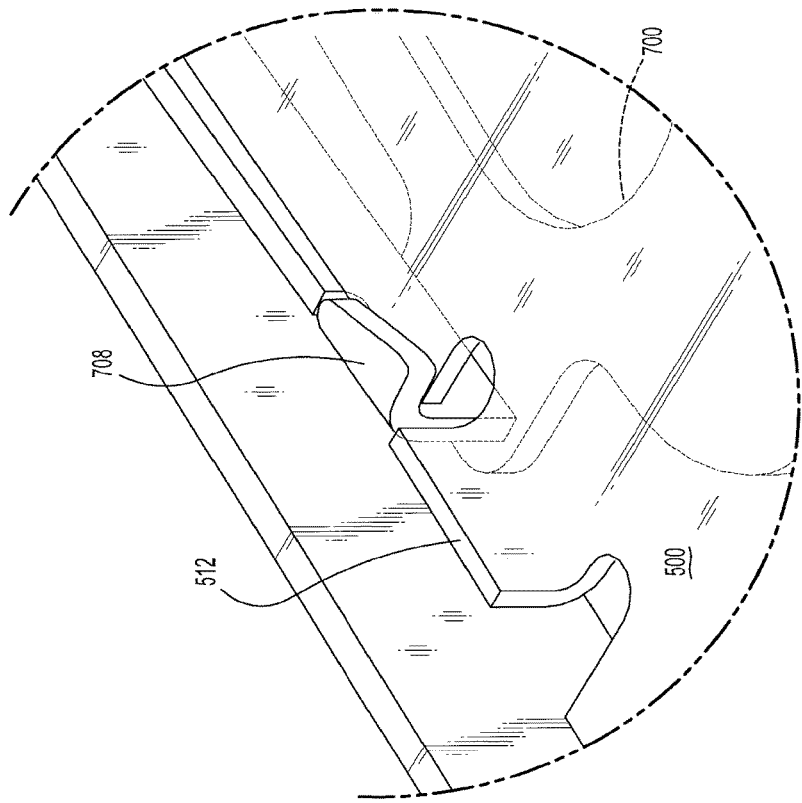
FIG. 24 is an enlarged top perspective view of the lockout engagement member extending through the separator plate in a first idle position with the lockout being shown below the separator plate for illustration.
Figure 23:
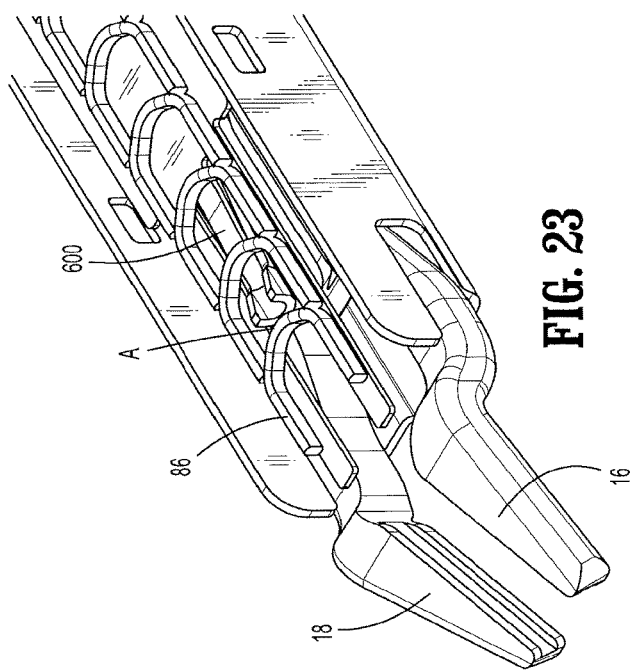
FIG. 23 is a top perspective view of the jaw body of the clip applying apparatus with the clip stack and the clip pusher shown in FIG. 8.

Referring now to the distal most exploded view of the jaw 16, 18 connected with the jaw body 800 shown as FIG. 23, the distal finger 604 of the clip pusher 600 contacts a distal most clip 86 at an apex A of the clip. In this manner, when the clip pusher 600 is advanced distally, the clip pusher 600 having the distal finger 604 will contact the apex "A" and move the clip in a distal most manner. FIG. 24 shows an enlarged area of detail of the clip applier 10. Here, advantageously the clip applier 10 may be fully locked out when there are few or no remaining clips in the stack 88 above the separator plate 500 or in any clip carrying channel.

In this manner, the surgeon cannot dry fire, or in other words fire the instrument without any clips in the stack 88. Referring again to FIG. 24, the separator plate 500 has the lockout member 512. The lockout member 512 is connected to the separator plate 500 or is integral with separator plate 500, and contacts the lockout engagement member 708. As the lockout engagement member 708 moves distally though the stroke, the lockout engagement member 708 will contact the lockout member 512 and the lockout engagement member's 708 distal movement is limited to allow for operation of the instrument.

Referring now to FIGS. 25 and 26, the clip applier 10 has the lockout 700 with the lockout engagement member 708 shown in the channel 68. The clip pusher 600 is disposed over the camming member 68. Referring now to FIG. 26, each of the lockout legs 704, 706 is biased and will mate with the notch 120 formed in the sidewall 122 of the camming member 46. The notch 120 is an orthogonally shaped slot. Notch 120 has a height suitable to permit the respective leg 704, 706 to enter or a portion to enter and be locked therein. Notch 120 also is narrow and does not permit the legs 704, 706 contact with the outer surface of the housing body 14. As the lockout 700 is advanced distally, the lockout legs 704, 706 will advance and enter the notch 120. Once the lockout legs 704, 706 enter into the notch 120, the lockout legs 704, 706 will be free from contact with the sidewalls 122 of the camming member 68 and spring outward toward opposite the sidewalls 122 and be biased in the notch 120. Thereafter, the legs 704, 706 are permanently retained in notch 120 and cannot escape therefrom.

Referring now to FIG. 25, the clip applier 10 also has a jaw locking member 66. The jaw locking member 66 is a resilient member that is connected by the pin or connector to the housing body 14 and has the arm 116 at a free distal end 118 that extends between the jaws 16, 18 of the jaw body 800. The jaw locking member 66 extends between the jaws 16, 18 and prevents the jaws 16, 18 from camming closed in a premature fashion. The free arm 116 at the distal end 118 of the jaw locking member 66 is rigid and resilient and extends between the jaws 16, 18.

Advantageously, the jaw locking member 66 can deflect relative to its original position and be stowed in a second lowered position when the engagement member 84 of the camming member 46 contacts and pushes the jaw locking member 66 to contact the outer cam surface 808 of the jaws 16, 18. Referring now to FIG. 26, the camming member 46 moves distally and engagement member 82 will cam down the arm 116 on the free distal end 118 of the jaw locking member 66 and provide that the jaw locking member 66 does not extend between the jaws 16, 18, and instead is below the jaws 16, 18. The camming member 46 will then cam the jaws 16, 18 closed without the jaw locking member 66 interfering. If the camming member 46 is not at the fully actuated or in the distal most position, then the jaw locking member 66 will remain between the jaws 16, 18, and thus prevent the jaws 16, 18 from accidentally be cammed closed. Thus, the clip applier 10 controls the jaws 16, 18 in an unactuated position to prevent stray movement which can slightly damage, knick or deform the distal most clip 86 as the clip 86 is advanced between the jaws 16, 18.

Operation of the clip applier 10 will now be described with reference to FIGS. 27 and 28 which show a side view and a top view of the clip applier 10 having the multiple subassemblies.

Referring to FIG. 29, there is shown a top view of the clip applier 10. FIGS. 29 and 30 illustrate the clip applier 10 prior to actuation of handles 22, i.e., in the prefired position. In the prefired position, the camming member 46 has the spring 60 connected to a proximal most portion of the handle housing 20. The spring 60 thus is connected to both the camming member 46 and the handle housing 20 and the spring 60 will urge the camming member 46 to its retracted position when the camming member 46 is advanced distally.

As shown, in FIG. 29, the pawl 56 is proximal relative to the rack 42. As the handles 22 are closed, the links 40a, 40b will be advanced to move the camming member 46 in a distal manner. The pawl 56 as being advanced will move past the rack 42. The pawl 56, if the handles 22 are released in mid stoke such as, for example, where the surgeon must attend to another surgical event and cannot complete the handle stroke, the finger 54 of the pawl 56 will engage with the teeth 136 of the rack 42 and thus prevent the camming member 46 from retracting proximally or moving freely distally and thus potentially damaging a clip being between the jaws 16, 18.

Referring now to FIG. 30, there is shown a lateral side cross sectional view of the clip applier 10 along line 30-30 of FIG. 29. As shown, the camming member 46 is connected to the spring 60, and the pawl 56 is connected through the camming member 46 as shown. The clip applier 10 further has the latch 48. As the camming member 46 is advanced distally due to the handles 22 being closed, the latch member 48 will also be driven distally and then will contact another engagement surface 96'. This contact between the latch 48 and the engagement surface 96' will cause the latch 48 to cam in a direction upwards against the surface 96'.

Referring now to FIG. 31, there is shown a cross sectional distal view of the clip applier 10. As shown, the clip applier 10 has the number of clips in the clip stack 88. As shown in the distal most region of the clip applier 10, the clip retainer spring 106 prevents the distal most clip 86 from being advanced in between the jaws 16, 18. Moreover, the curved or bent clip portion 108 of the clip retainer spring 106 extends below the clip. As shown in cross section, the engagement member 84 connected to the camming member 46 is in a proximal most position being unfired. Moreover, the lockout 700 is also in a proximal most position.

Referring to FIG. 32, there is shown a top view of the clip pusher 600 with finger 604 being near an apex of the distal most clip 86. The clip pusher 600 (upon being advanced) will advance the distal most clip 86 underneath the curved clip member 108 of the clip retainer spring 106 (FIG. 31) and then be able to travel further distally in order to travel between the jaws 16, 18. One should appreciate that upon manipulating the clip applier 10 not by the handles 22, (by simply picking up the clip applier 10 prior to use or by simply resting the clip applier 10 before use on a table) one cannot overcome the bias of the clip retainer spring 106 and the clips will be held in the stack 88 until the clip applier 10 is fired.

Referring back to FIG. 31, as can be seen the jaw locking member 66 has the blocking arm 116 portion that is extending between the jaws 16, 18. Here, if the orientation of the clip applier 10 is disturbed, the jaws 16, 18 will not close or move relative to one another and will be prevented from doing so because of the arm 116 of the jaw locking member 66 that extends upward. The engagement member 84 as it is advanced distally will cam down the jaw locking member 66 and then permit the jaws 16, 18 to be free and move relative to one another and compress a clip disposed therebetween.

FIG. 33 shows the relative placement of the lockout 700 having the lockout legs 704, 706 and the notch 120 in the camming member 46. The lockout spring 724 is connected to the lockout 700 through the spring aperture 712 as shown in FIG. 22 in order to bias the lockout member 700 relative to the separator plate 500. Referring to a distal most portion of the figure, as shown the camming member 46 has the notches 120 in a lateral side.

As can be understood as the lockout 700 is moved distally, the lockout legs 704, 706 will mate into the notch 120 of the camming member 46 and thus prevent further distal movement of the lockout member 700. Referring to a top view of the clip applier 10 shown in FIG. 34, the lockout engagement member 708 shown in phantom dotted lines is under the separator plate 500 and also extends upward to a position adjacent the body housing 14. The lockout engagement member 708 will lock the lockout 700 and the camming member 46 at a predetermined line of demarcation such as when there are few clips remaining.

Referring to a proximally located original position, the clip follower 300 is disposed in a proximal most position as shown behind and advancing the clips distally from the stack 88 to be fired. Referring now to FIGS. 35 and 36, there is shown the clip follower 300 with the spring 400 being disposed behind the clip follower 300. As shown, the latch member 48 cams upwardly in direction being about perpendicular to the driving of the camming member 46. Referring to FIG. 36, the follower 300 is shown biasing the proximal most clip 104 in the clip stack 88.

Figure 37:
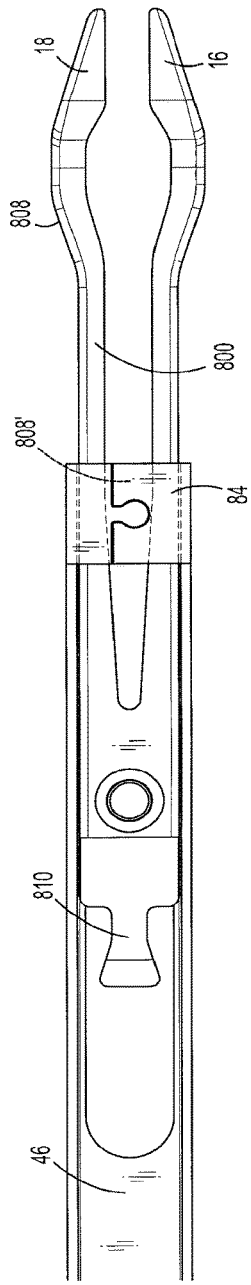
FIG. 37 is a view of the camming plate and the jaws.

FIG. 37 shows the orientation of the engagement member 84 and the jaws 16, 18 on the jaw body 800. As can be seen from the figure, the jaw body 800 has the outer camming surface 808. The outer camming surface 808 is curved slightly and defines an outer surface of the jaws 16, 18 on the jaw body 800. The engagement member 84 is a rectilinear member having an interior space 808' that fits over the outer camming surface 808 of the jaws 16, 18.

The engagement member 84 will be advanced distally, and contact the outer camming surface 808 of the jaws 16, 18. As the camming member 46 progresses through the stroke, the engagement member 84 contacts the outer camming surface 808 of the jaws 16, 18 and forces the camming surface 808 in a direction inwardly by the contact. Thus, the jaw body 800 connected to the housing body 14 will not move and thus force close the jaws 16, 18. The jaws 16, 18 in turn apply a compressive force to the clip therebetween.

Figure 39:
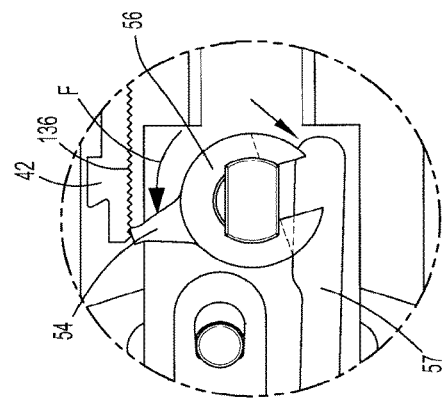
FIG. 39 is an enlarged view of the pawl, pawl spring and rack of the handle portion that prevent the cam plate from retracting in mid-stroke.
Figure 38:
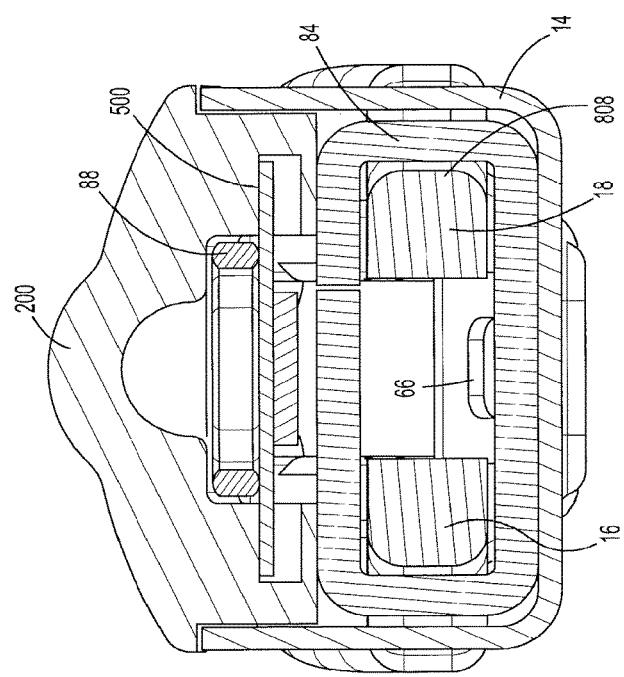
FIG. 38 is front cross sectional view of the body portion along line 38-38 of FIG. 31 with a cover, a clip stack, a stationary plate, a cam plate and the jaws in cross section to show placement thereof.

Referring to FIG. 38, there is shown a cross sectional view of the channel 68 of the clip applier 10. As shown, in cross section, the clip applier 10 has the distal most clip 86 above the separator plate 500. The jaws 16, 18 of the clip applier 10 are in the distal most portion of the view in the unactuated state. As can be seen the jaw locking member 66 is disposed between the jaws 16, 18 to prevent any accidental compression or closing of the jaws 16, 18. Further, the clip applier 10 has the engagement member 84 in an unactuated state, or disposed proximal relative to the outer cam surface 808 of the jaws 16, 18. As the engagement member 84 is driven distally the engagement member 84 will contact the outer camming surface 808 of the jaws 16, 18 to compress the jaws 16, 18 and compress the clip advanced between the jaws 16, 18. In this view, the outer camming surface 808 is proximal and behind the jaws 16, 18. Referring to FIG. 39, as the handles 22 are closed, the pawl spring 56 drives the pawl 56 in the direction of reference arrow "F" and the pawl finger 54 contacts the teeth 136 of the rack 42. As the pawl finger 54 contacts the teeth 136 of the rack 42, the pawl 56 maintains the camming member 46 in position to prevent an accidental or a partial actuation of the engagement member 84. Instead, the finger 54 of the pawl 56 will (when the handles 22 are released) maintain a position being disposed between the teeth 136 of the rack 42. This allows the pawl 56 to remain in position until the handles 22 are further closed or compressed where the pawl 56 will then be further advanced over the teeth 136 of the rack 42.

Figure 41:
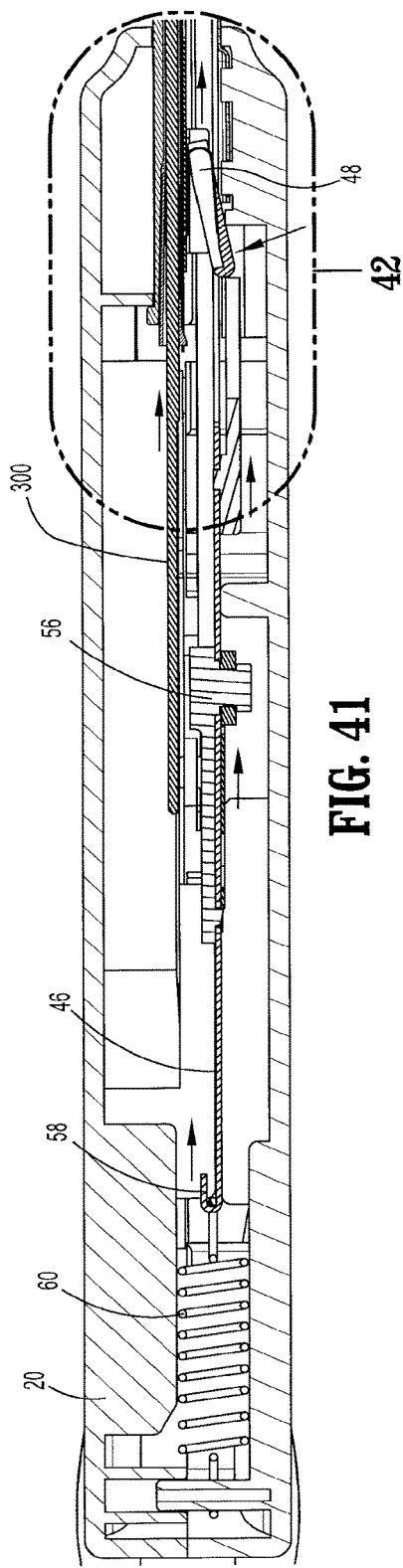
FIG. 41 is a cross sectional view of the cam plate being advanced distally.

FIG. 40 shows the beginning of the stroke. The handles 22 are compressed in a scissor like fashion in a direction B toward the handle body 20. In this manner, the links 40a, 40b will move the camming member 46 in a distal manner, as shown by reference arrow "C". As shown in FIG. 39, the pawl 56 and rack 42 will maintain the camming member 46 in an intermediate position if the handles 22 are prematurely released in mid-stroke. FIG. 41 shows a cross sectional side view of the clip applier 10 at the beginning of the stroke. As can be seen, the camming member 46 is connected by the stretched spring 60 to the housing 20. As shown in the proximal section, the camming member 46 is connected to the spring 60 by the hook 58 and the spring 60 is also connected to the housing 20.

Figure 42:
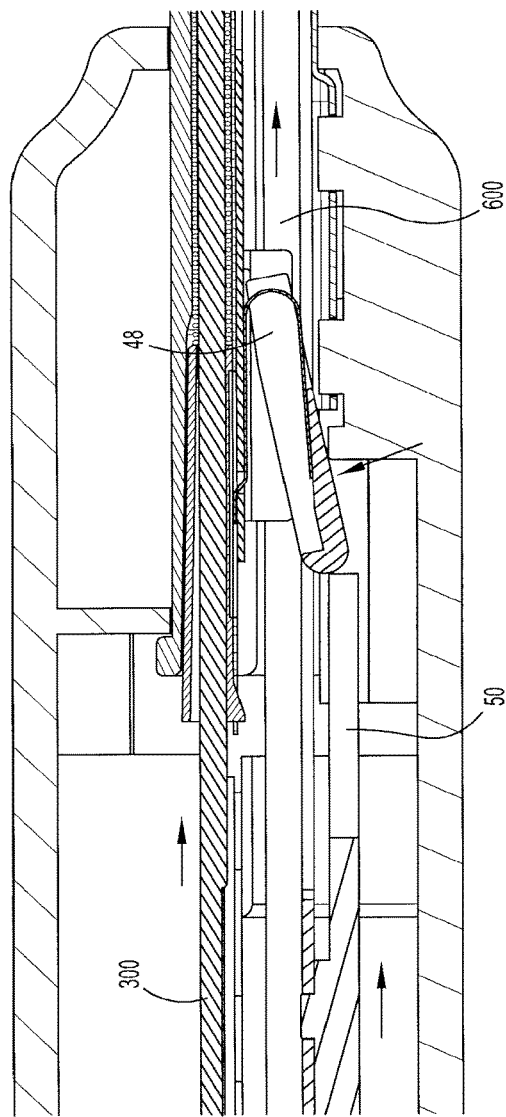
FIG. 42 is a cross sectional view of the clip follower, the latch driver, the latch and latch spring being advanced distally.

As can be understood, the spring 60 biases the camming member 46 to return to the original proximal most position once the handle are released. FIG. 42 shows an enlarged detail of the reference circle 42 shown in FIG. 41. FIG. 42 shows the clip follower 300 being disposed above the latch driver 50 and the latch 48. As the camming member 46 is advanced distally, the camming member 46 will also urge the latch driver 50 distally. The latch driver 50 upon being moved distally will advance the latch 48 to move in a perpendicular direction relative to the movement of the camming member 46. This will urge the clip pusher 600 to move distally.

Figure 43:
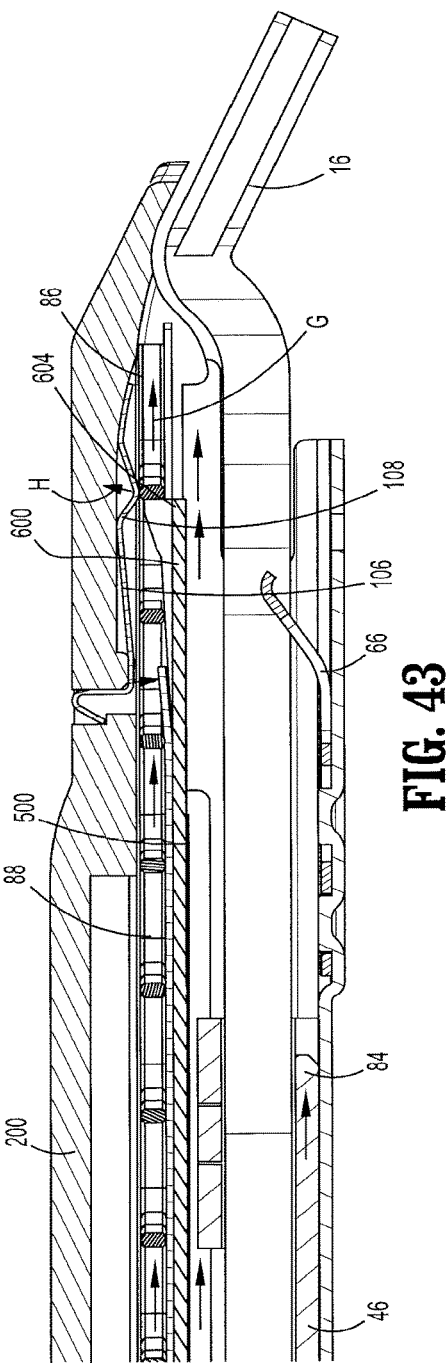
FIG. 43 is a cross sectional view of the body portion with the clip retainer spring, the jaw safety and the clip pusher being advanced distally with the distal most clip being advanced distally past the clip retainer spring.
Figure 44:
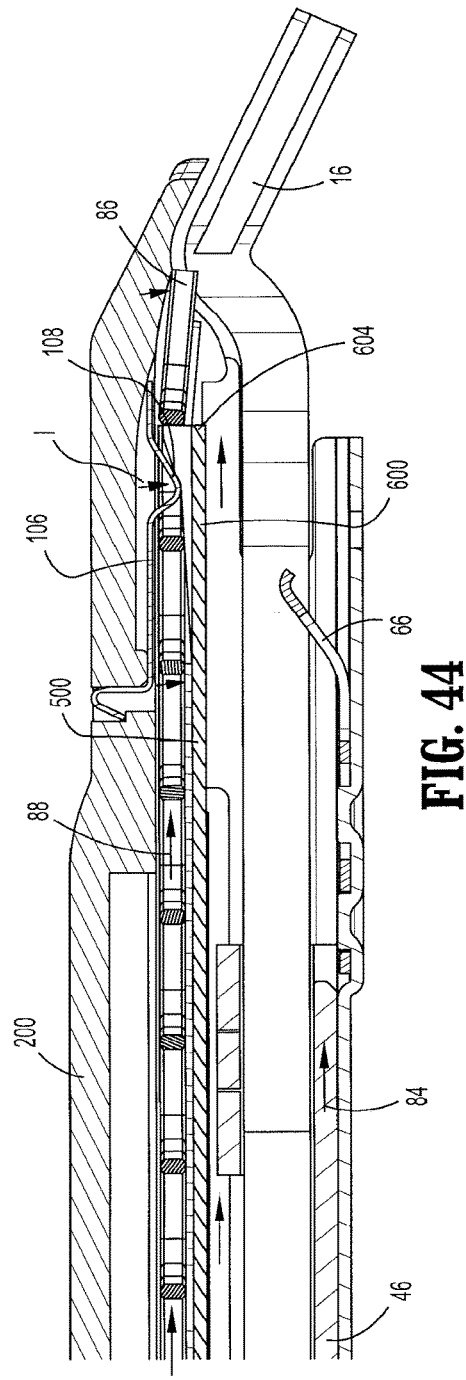
FIG. 44 is a cross sectional view of the clip retainer spring moving back to an original position to prevent the stack from moving distally as shown in FIG. 43.

Referring now to a distal most section of the clip applier 10, shown in cross section in FIG. 43, the clip pusher 600 will advance the distal most clip 86 past the curved clip member 108 of the clip retaining spring 106 as shown by reference arrow "G". As can be understood, the clip retaining spring 106 will be deflected upward in the direction of the reference arrow "H". In this manner, the clip pusher 600 can advance the distal most clip 86 in a direction toward the jaws 16, 18, and the clip retaining spring 106 will then deflect downward as shown by reference arrow "I" in FIG. 44 and the curved clip member 108 of the clip retaining spring 106 will then be advanced back into the path of the next clip to then terminate the movement of the next clip and prevent the next clip from interfering with the operation of the clip applier 10 as shown in FIG. 44. Referring once again to FIG. 43, the engagement member 84 of the camming member 46 is shown in a first proximal position relative to the outer camming surface 808 of the jaws 16, 18 and the jaw locking member 66. Referring to FIG. 44, the camming member 46 is then advanced further distally, and thus further advances the engagement member 84. One should appreciate that the jaw locking member 66 in this position prevents any actuation of the jaws 16, 18, as the jaw locking member 66 has the arm 116 that is disposed between the jaws 16, 18 to prevent the jaws 16, 18 from closing.

Figure 45:
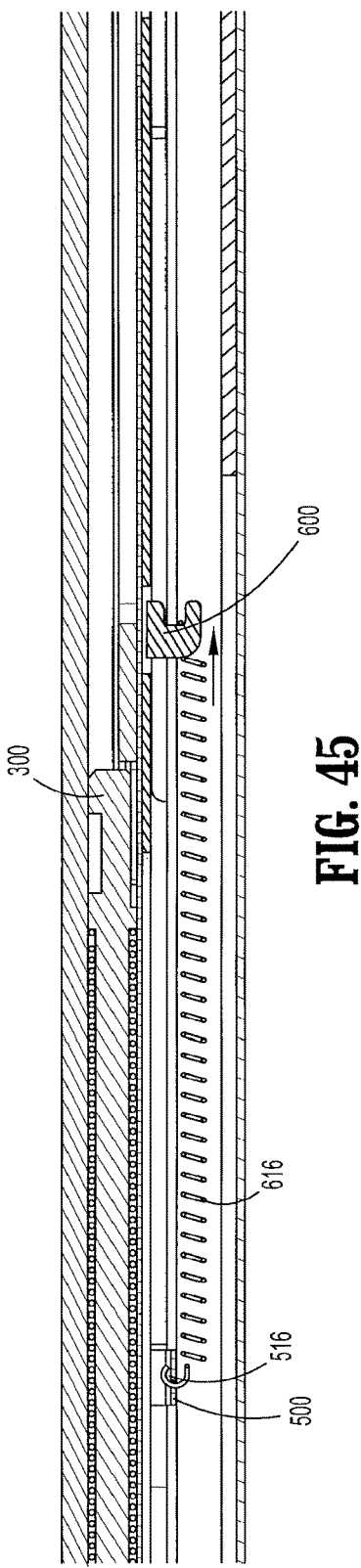
FIG. 45 is a cross sectional view of the body portion showing the clip pusher and pusher spring in an elongated state being connected to the stationary plate.

Referring now to FIG. 45, the clip follower 300 is shown being disposed above the clip pusher 600. The clip pusher 600 further has a hooked portion connected to the spring 616 that connects to the second hook 516 of the separator plate 500. The spring 616 is connected to the stationary separator plate 500 to bias the clip pusher 600. In this manner, the spring 616 once elongated biases the clip pusher 600 to the original proximal most position.

Figure 46:
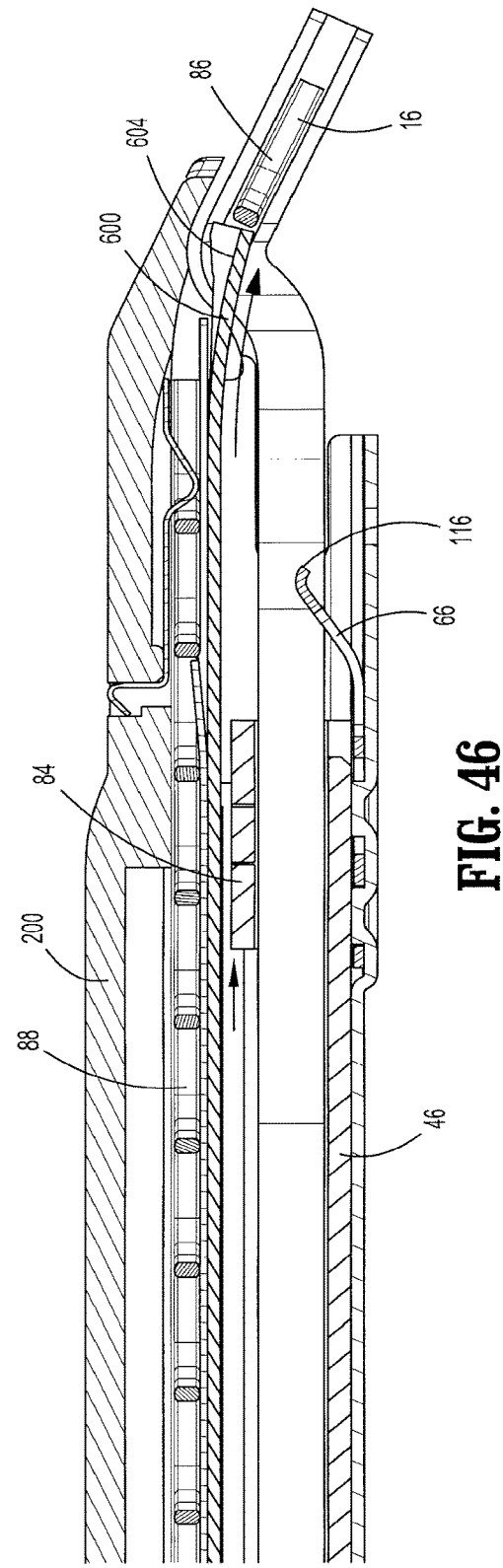
FIG. 46 is a cross sectional view of the clip pusher advancing the distal most clip between the jaws and the jaw safety having a free end disposed between the jaws.

Referring now to FIG. 46, as the camming member 46 is further moved through the stroke, the clip pusher 600 continues to advance the distal most clip 86 between the jaws 16, 18.

The camming member 46 also further moves the engagement member 84 further in a distal most direction. As can be seen from FIG. 46, the engagement member 84 is closer and adjacent to the jaw locking member 66 to deflect the arm 116 in a direction downward and to move the arm 116 of the jaw locking member 66 from between the jaws 16, 18 to beneath the jaws 16, 18.

Referring now to FIG. 47, one can appreciate that now the distal most clip has been loaded in between the jaws 16, 18, the clip pusher 600 is free to retract so as to permit other assemblies of the clip applier access to the loaded jaws 16, 18 to compress the clip. FIG. 47 shows the latch driver 50. At this predetermined demarcation line of the stroke, the latch driver 50 will cam the latch 48 (to contact the abutment 96') and cam the latch 48 out of engagement of the latch driver 50. Referring to FIG. 48, the latch 50 and clip pusher 600 free of contact with the latch driver 50 will now traverse proximally out of engagement with the latch driver 50 and retract. The engagement member 84 and the latch driver 50 will continue to traverse distally.

Referring to FIG. 48, as camming member 46 and clip pusher 600 advance within the channel 68, the tension in the latch 48 is increased, i.e., spring 94 and the latch 48 is cammed out of engagement with the driver 50 and will retract. When distal-most clip 86 is fully positioned within jaws 16 and 18, the latch driver 50 disengages a distal end of latch 48 and pivots latch 48 in the direction indicated by arrow "J" (FIG. 47) to release the latch member 48 from the abutment member 96' (FIG. 48). When latch member 48 is released from abutment member 96', the latch spring 94 returns the clip pusher 600 to its retracted position.

Figure 49:
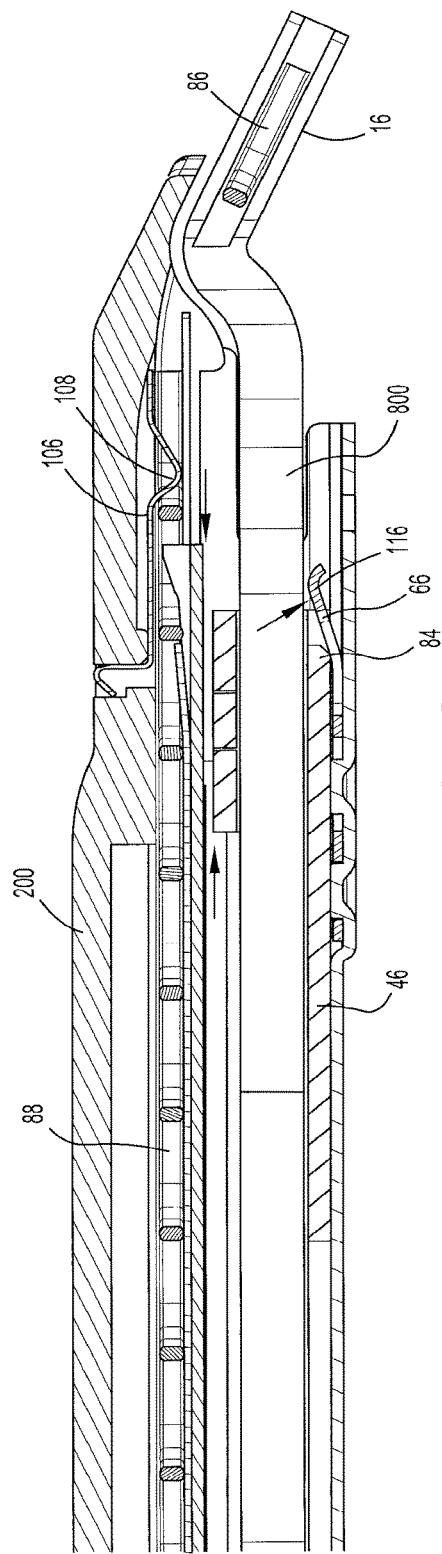
FIG. 49 is a cross sectional view of the clip pusher being retracted proximally with the cam plate deflecting the jaw safety free end from between the jaws to allow the cam plate to close the jaws.
Figure 50:
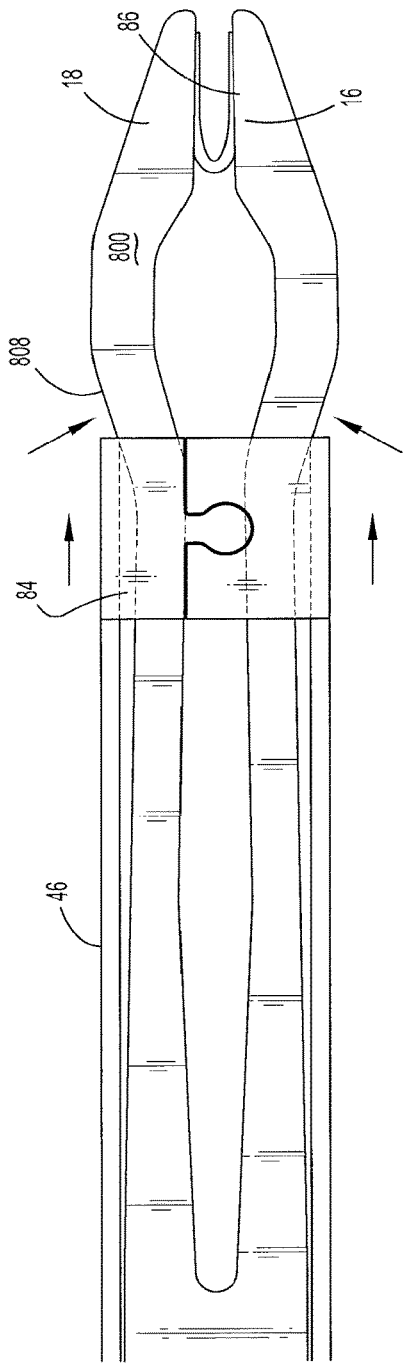
FIG. 50 is a distal view of the cam plate contacting the outer surface of the jaws for closing the jaws and a clip between the jaws.

Referring now to FIG. 49, as the handles 22 are more fully actuated, i.e., moved closer to housing 20, the engagement member 84 engages arm 116 of the jaw locking plate 66. The engagement member 84 will then deflect the jaw locking plate 66 in a direction downwardly from between legs 804, 806 of the jaws body 800. The continued advancement of the camming member 46 advances the engagement member 84 into the outer camming surfaces 808 of jaws 16 and 18 to move jaws 16 and 18 from a spaced apart position to a crimping position as shown in FIG. 50.

Referring to FIG. 51, as the camming member 46 is moved from its retracted position within housing body 14 to the advanced position, a finger of the pawl 56 engages teeth 136 of the rack 42 to prevent the pawl spring 54 from returning the camming member 46 to its retracted position when the handles 22 are released part way. As such, once handles 22 begin to be actuated and the pawl finger 54 engages the rack 42 (FIG. 51) the camming member 46 cannot be returned to its retracted position until clip applier 10 is fully actuated.

When the camming member 46 is moved to its advanced position, the pawl 56 passes by a distal most end of rack 42 as shown in FIG. 52 and cantilevered or spring arm 158 of the pawl spring 57 rotates pawl 56 in the direction indicated by arrow "K" in FIG. 52 to a position in which finger 54 of pawl 56 is positioned at about 90 degrees relative to the camming member 46. Thus, when the handles 22 are released and the spring 60 returns the camming member 46 to a retracted positioned, the finger 54 will engage the distal end of rack 42 and rotate counter-clockwise in the direction indicated by the opposite of arrow "K" in FIG. 52 and ratchet over teeth 136 of the rack 42. Note, in the fully retracted position of the camming member 46, the pawl 56 is positioned proximally of rack 42. In this position the pawl spring 57 returns the finger 54 of pawl 56 to the 90 degree position relative to the camming member 46.

Referring now to FIG. 53, the engagement member 84 is advanced to its distal most position and contacts the outer camming surfaces 808 of the jaws 16, 18 to close the jaws 16, 18 and compress a clip therebetween. FIG. 54 shows the clip 86 compressed around a vessel for occluding the vessel. Referring now to FIG. 55, the handles 22 being released will permit the spring 60 to impart a force to the camming member 46 in the proximal direction "L" in order to retract the camming member 46 to it initial position for firing of the next clip.

FIG. 56 shows the clip applier 10 with a novel lockout mechanism that will lockout the clip applier 10 after the last or a predetermined last clip is fired from the clip applier 10. This is especially advantageous as the clip applier 10 is not dry fired or fired without any further clips in the clip applier 10. The lockout mechanism provides the clip applier 10 with a tactile feedback to the surgeon that the clip applier 10 is out of clips and a new full clip applier is needed.

Referring now to the reference circle 57 shown in FIG. 56, the clip follower 300 has the lockout tab 314. As discussed previously, the lockout tab 314 is disposed on a lateral proximal side 316 of the clip follower 300. The lockout 700 also has a lockout engagement member 708 that extends upwardly through the channel 68. In a normal state of operation of the clip applier 10, the lockout engagement member 708 cannot traverse past the lockout member 512 on the stationary plate 500, and is blocked from moving distally.

Figure 58:
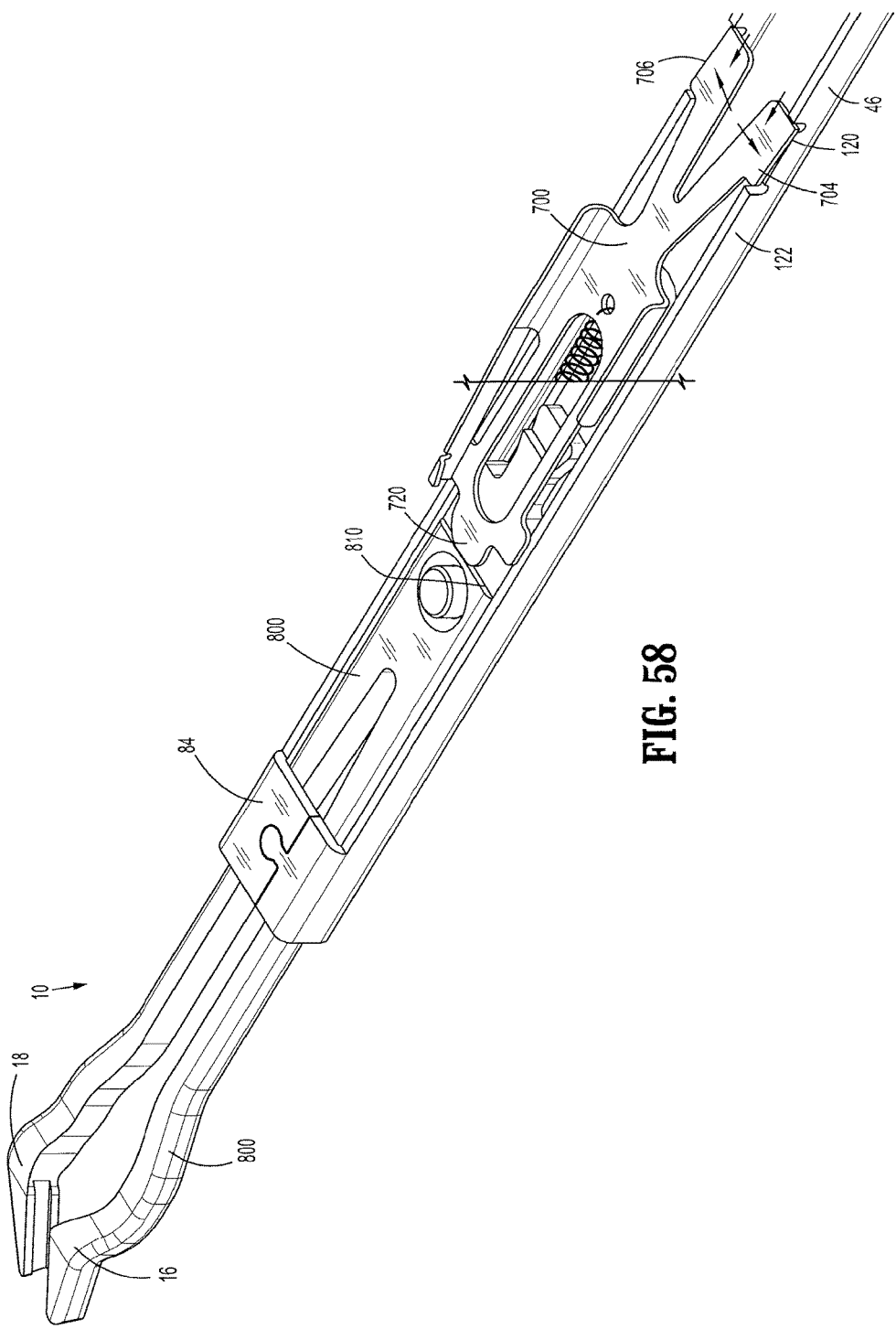
FIG. 58 is a perspective view of the lockout member having the flexible legs advancing into the slots of the cam plate and the lockout tab engaging a surface on the jaws to lockout the clip applier and to prevent further distal movement of the cam plate and further actuation of the handle portion.

The follower 300 (at a predetermined line of demarcation once a number of clips of the stack 88 have been exhausted and fired from the clip applier 10) will move distally given that the number of clips in the stack 88 has been reduced. The clip applier 10 has the lockout tab 314 that will contact a sloping surface 750 of the lockout engagement member 708 and move the lockout engagement member 708 outward in the direction of reference arrow M. Once the lockout engagement member 708 moves outwardly, the lockout engagement member 708 can now move distally or past the lockout member 512 on the separator plate 500 in the direction of reference arrow P. The clip follower 300 thus moves the lockout engagement member 708 in a distal most direction as indicated by reference arrows "M" and "P" on FIG. 58.

The legs 704, 706 of the lockout 700 will then move outwardly and into the notch 120 being formed on the camming member 46. In this manner, the lockout legs 704, 706 snaps into the notch 120 and cannot be removed therefrom.

Further, the lockout 700 has a rounded distal end tab 720 that mates with a stepped down stop member 810 on the jaw body 800. This interface prevents the lockout engagement member 708 and the camming member 46 from moving distally and thus lockouts out the clip applier 10 and prevents and further operation of the engagement member 46, the clip pusher 600 and the clip follower 300. Instead, the handles 22 will be fixedly in place and when squeezed will provide the surgeon will a great deal of tactile resistance. This will provide the surgeon with an indication that the instrument 10 has no remaining clips, needs to be discarded and replaced with a fresh clip applier 10.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An apparatus for applying surgical clips comprising:
a clip stack; and
a body portion housing the clip stack, the body portion including:
a clip follower slidably supported therein, wherein the clip follower is positioned proximally of the clip stack and biased to engage the clip stack, the clip follower defining a tab extending from a lateral side of the clip follower;
a separator plate fixedly supported therein, wherein the separator plate defines a first projection; and
a lockout having a lockout engagement member, the lockout being selectively movable:
from a first position, wherein the lockout engagement member contacts the first projection of the separator plate to limit distal movement of the lockout;
to a second position, wherein the tab of the clip follower selectively engages the lockout engagement member of the lockout such that the lockout engagement member clears the first projection of the separator plate to enable distal movement of the lockout.

2. The apparatus according to claim 1, wherein the body portion further comprises:
a clip pusher slidably supported therein; and
a camming member slidably supported therein, wherein the camming member defines a first notch therein, the lockout being movable from the first position in slidable relation to the camming member to the second position interlocked with the first notch of the camming member, wherein the clip follower actuates the lockout to the second position when the clip follower advances to a predetermined clip in the clip stack.

3. The apparatus according to claim 2, wherein the lockout further includes a first leg, wherein in the second position of the lockout, the first leg of the lockout projects into the first notch of the camming member to interlock the lockout and the camming member, thereby limiting distal movement of the camming member.

4. The apparatus according to claim 3, wherein the lockout includes a second leg opposing the first leg, the first and second legs each including a stop member projecting therefrom, and wherein the camming member includes a second notch opposing the first notch, the first and second notches of the camming member each being configured to receive a respective one of the stop members of the first and second legs.

5. The apparatus according to claim 2, further comprising a jaw body fixedly supported at a distal end of the body portion, the jaw body having a pair of jaws fixedly supported at a distal end of the jaw body and a stop member fixedly supported at a proximal end of the jaw body, the stop member including a stepped down surface;
wherein the clip pusher is operable to advance a distal-most clip of the clip stack to a position between the pair of jaws;
wherein the camming member is operable to approximate the pair of jaws to deform the distal-most clip positioned between the pair of jaws; and
wherein the clip follower is operable to urge the clip stack distally towards the pair of jaws.

6. The apparatus according to claim 5, wherein the lockout further includes a tab extending from a distal end thereof, the tab having a downward curved profile configured to engage the stepped down surface of the stop member of the jaw body when the lockout is in the second position.

7. The apparatus according to claim 6, wherein when the lockout is in the second position and each of the stop members of the first and second legs are received within the respective first and second notches of the camming member, engagement between the tab of the lockout and the stepped down surface of the stop member of the jaw body prevents distal advancement of the camming member.

8. The apparatus according to claim 5, further comprising a clip retainer member configured to maintain the clip stack proximally, the clip retainer member limiting movement of the clip stack so only a distal most clip is advanced between the pair of jaws by the clip pusher.

9. The apparatus according to claim 5, further comprising a jaw locking member having a cantilevered free end and a fixed end connected to the body portion, wherein when the cantilevered free end of the jaw locking member extends between the pair of jaws, compression of the pair of jaws is prevented, and wherein the cantilevered free end is adapted to be deflected about the fixed end thereof to permit the pair of jaws to be closed.

10. The apparatus according to claim 2, wherein the lockout engagement member of the lockout includes a sloping surface, wherein as the tab of the clip follower engages the sloping surface of the lockout engagement member, the lockout engagement member is urged in an outward direction relative to the first projection of the separator plate, thereby clearing the first projection of the separator plate to enable distal movement of the lockout.

11. The apparatus according to claim 2, wherein the clip follower actuates the lockout engagement member when the clip follower advances to one of:
a last clip in the clip stack;
a second to last clip in the clip stack; or
a third to last clip in the clip stack.

12. The apparatus according to claim 1, wherein the separator plate includes a second projection and the body portion further includes a lockout spring coupling the second projection of the separator plate and the lockout, the lockout spring configured to bias the lockout relative to the separator plate.

13. An apparatus for applying surgical clips comprising:
a clip stack; and
a body portion housing the clip stack, the body portion including:
a clip follower slidably supported therein, wherein the clip follower is positioned proximally of the clip stack and biased to engage the clip stack, wherein the clip follower includes a distal end, a proximal end and a body therebetween;

a camming member slidably supported therein, wherein the camming member defines at least one aperture therein, the camming member biased to a first position; and a pair of jaws fixedly supported at a distal end of the body portion; and a handle portion extending proximally from the body portion, the handle portion including:

a trigger assembly pivotably coupled thereto;

a cam spring coupled to a proximal portion of the handle portion and a portion of the camming member, wherein the cam spring is provided with a bias to urge the camming member to a first position; and a ratchet mechanism at least partially mounted on the camming member, wherein the ratchet mechanism includes:

a pawl rotatably mounted in the at least one aperture of the camming member; and a rack supported within a recess of the handle portion, the rack including a plurality of rack teeth, wherein the pawl is positioned such that the ratchet mechanism is configured to engage the plurality of rack teeth to retain the camming member in a partially advanced position against the bias of the cam spring during actuation of the trigger assembly.

14. The apparatus according to claim 13, wherein the ratchet mechanism further includes a pawl spring mounted on the camming member, the pawl spring biasing the pawl into engagement with the plurality of rack teeth of the rack.

15. The apparatus according to claim 14, wherein the pawl includes a stepped side on a bottom surface thereof and the pawl spring includes a spring arm, the spring arm of the pawl spring being positioned to engage the stepped side of the pawl to urge the pawl into engagement with the plurality of rack teeth of the rack.

16. The apparatus according to claim 15, wherein the ratchet mechanism further includes a plate extension mounted on a bottom surface of the camming member, the plate extension having a pivot member extending therefrom and through the at least one aperture of the camming member to rotatably mount the pawl on the camming member.

17. The apparatus according to claim 13, further comprising a lockout member includes a distal end, a proximal end and a body therebetween, wherein the lockout member being movable from a first position in slidable relation to the camming member to a second position interlocked with the camming member, wherein in the second position, the lockout member is provided to engage the camming member to limit distal movement of the camming member; and wherein the clip follower actuates the lockout member when the clip follower advances to a predetermined clip in the clip stack.

18. The apparatus according to claim 17, wherein the lockout member includes a flexible leg having a stop member, and wherein the camming member includes at least one notch sized and dimensioned to receive the stop member of the lockout member to interlock the lockout member and the camming member.

19. The apparatus according to claim 17, wherein the clip follower has a lockout nub projecting from a lateral side thereof, and wherein the lockout nub of the clip follower engages the lockout member to move the lockout member from the first position to the second position.

* * * * *